United States Patent [19]
Wang et al.

[11] Patent Number: 5,843,937
[45] Date of Patent: Dec. 1, 1998

[54] DNA-BINDING INDOLE DERIVATIVES, THEIR PRODRUGS AND IMMUNOCONJUGATES AS ANTICANCER AGENTS

[75] Inventors: Yuqiang Wang, Mountain View; Susan C. Wright, Saratoga; James W. Larrick, Woodside, all of Calif.

[73] Assignee: Panorama Research, Inc., Mountain View, Calif.

[21] Appl. No.: 652,883

[22] Filed: May 23, 1996

[51] Int. Cl.$^6$ .............. A61K 31/40; A61K 31/545; C07D 487/04; C07D 501/22
[52] U.S. Cl. .............. 514/202; 514/23; 514/32; 514/43; 514/259; 514/283; 514/371; 514/372; 514/377; 514/387; 514/397; 514/407; 514/410; 514/411; 536/17.3; 536/28.6; 536/115; 540/222; 548/181; 548/233; 548/245; 548/246; 548/265.4; 548/304.1; 548/311.7; 548/312.1; 548/364.7; 548/421; 548/425; 548/427; 548/428; 548/433
[58] Field of Search .............. 548/427, 304.1, 548/421, 425, 433; 514/411, 202, 387, 410; 540/222

[56] References Cited

U.S. PATENT DOCUMENTS 5,502,068  3/1996  Lown et al. .............. 514/397

OTHER PUBLICATIONS

Boger, Dale L., et al.; "Duocarmycin SA Shortened, Simplified, and Extended Agents: A Systematic Examination of the Role of the DNA Binding Subunit"; *J. Am. Chem., Soc,*; 119:4977–4986 (1997).

P. Aristoff et al., *Advances in Medicinal Chemistry*, 2:67–110 (1993).

P. Aristoff et al., *J. Med. Chem.*, 36:1956–1963 (1993).

D. Boger et al., *Bioorganic & Medicinal Chemistry*, 3(6):611–621 (1995).

D. Boger et al., *Bioorganic & Medicinal Chemistry*, 3(6):761–775 (1995).

D. Boger et al., *Bioorganic & Medicinal Chemistry*, 3(11):1429–1453 (1995).

D. Boger et al., *J. Am. Chem. Soc.*, 112:4623–4632 (1990).

D. Boger et al., *J. Am. Chem. Soc.*, 116:7996–8006 (1994).

D. Boger et al., *Proc. Natl. Acad. Sci. USA*, 92:3642–3649 (Apr. 1995).

R. Chari et al., *Cancer Research*, 55:4079–4084 (1995).

N. Fregeau et al., *J. Am. Chem. Soc.*, 117:8917–8925 (1995).

L. Hurley et al., *J. Am. Chem. Soc.*, 112:4633–4649 (1990).

Y. Wang et al., *Book of Abstracts*, 209th ACS National Meeting, Apr. 2–6, 1995, Anaheim, California.

Y. Wang et al., *J. Med. Chem.*, 31:590–603 (1988).

Y. Wang et al., *Anti–Cancer Drug Design*, 11:15–34 (1996).

*Primary Examiner*—Richard L. Raymond
*Attorney, Agent, or Firm*—Townsend and Townsend and Crew LLP

[57] ABSTRACT

The present invention relates to novel DNA alkylating agents and the prodrugs of these agents which are useful as antitumor agents and DNA labelling agents. The compounds are hydroxy dihydrobenzindole oligopeptides and prodrugs thereof wherein the monomeric constituents are derived from monocyclic or bicyclic heterocyclic aromatic residues.

41 Claims, 14 Drawing Sheets

| Compound | | IC$_{50}$ (nM) |
|---|---|---|
| YW-242, A = | C(=O)-[indoline]-NH$_2$ | 0.09 |
| YW-198, A = | C(=O)-[indoline]-NHCOCH$_3$ | 0.2 |
| YW-200, A = | (C(=O)-[indoline]-NHCOCH$_3$)$_2$ | 0.01 |
| YW-201, A = | C(=O)-[indoline]-NHCO-[benzofuran]-NHCOCH$_3$ | 0.07 |
| YW-202, A = | C(=O)-CH=CH-[indoline]-NHCOCH$_3$ | 0.2 |
| YW-215, A = | C(=O)-CH=CH-[indoline]-NHCO-[benzofuran] | 0.09 |
| YW-231, A = | C(=O)-[indoline]-NHCO(CH$_2$)$_3$OH | 0.6 |
| YW-254, A = | (C(=O)-[indoline]-NHCO(CH$_2$)$_3$OH)$_2$ | 0.1 |
| YW-259, A = | (C(=O)-[indoline]-NHCO(CH$_2$)$_3$OH)$_3$ | 0.08 |

| Compound | | IC$_{50}$ (nM) |
|---|---|---|
| YW-247, A = | [structure with indoline-C(=O)-, NHCO(CH$_2$)$_3$O- linked to sugar with CO$_2$Me, OAc, OAc, AcO] | 1.4 |
| YW-249, A = | [structure: (indoline-C(=O))$_2$ with NHCO(CH$_2$)$_3$O- sugar CO$_2$Me, OAc, OAc, AcO] | 0.55 |
| YW-258, A = | [structure: (indoline-C(=O))$_3$ with NHCO(CH$_2$)$_3$O- sugar CO$_2$Me, OAc, OAc, AcO] | 0.09 |
| YW-235, A = | [indoline-C(=O)- NHCO(CH$_2$)$_4$- biotin moiety] | 0.7 |
| YW-285, A = | [indoline-C(=O)- NHCOOCH$_2$- cephalosporin S-oxide with NHCOCH$_2$-thiophene, COOH] | 0.9 |
| YW-286, A = | [N-methyl pyrrolidine-C(=O)- with NO$_2$] | 5.5 |
| YW-284, A = | [N-methyl pyrrolidine-C(=O)- with NH$_2$] | 9.0 |

FIG. 9
CONTINUED

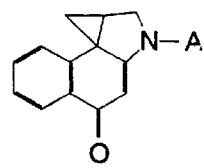

| Compound | | IC$_{50}$ (nM) |
|---|---|---|
| YW-161, A = | (pyrrolidine with NHCOCH$_3$, N-CH$_3$, C=O) | 5.0 |
| YW-222, A = | C(=O)—CH—CH—(pyrrolidine with NHCOCH$_2$CH$_2$CH$_3$, N-CH$_3$) | 0.5 |
| YW-210, A = | C(=O)—(octahydroindole with NHCOCH$_3$) | 0.3 |
| YW-212, A = | (C(=O)—octahydroindole with NHCOCH$_3$)$_2$ | 0.05 |
| YW-213, A = | C(=O)—(octahydroindole)—NHCO—O—(benzofuran with NHCOCH$_3$) | 0.2 |
| YW-214, A = | C(=O)—CH—CH—(octahydroindole with NHCOCH$_3$) | 0.6 |
| YW-216, A = | C(=O)—CH—CH—(octahydroindole)—NHCO—O—(benzofuran) | 0.09 |
| Doxorubicin | | 0.10 |

*FIG. 9*
CONTINUED

DNA-BINDING INDOLE DERIVATIVES, THEIR PRODRUGS AND IMMUNOCONJUGATES AS ANTICANCER AGENTS

BACKGROUND OF THE INVENTION

The present invention relates to novel DNA alkylating agents and the prodrugs of these agents which are useful as antitumor agents and DNA labelling agents.

CC-1065 (FIG. 1) was first isolated from *Streptomyces zelensis* in 1981 by the Upjohn Company (Hanka et al., *J. Antibiot.* (1978) 31:1211; Martin et al., *J. Antibiot.* (1980) 33:902; Martin et al., *J. Antibiot.* (1981) 34:1119) and was found to have potent antitumor and antimicrobial activity both in vitro and in experimental animals (Li et al., *Cancer Res.* (1982) 42:999; Martin et al. (1981)). CC-1065 binds to double-stranded B-DNA within the minor groove (Swenson et al., *Cancer Res.* (1982) 42:2821) with the sequence preference of 5'-d(A/GNTTA)-3' and 5'-d(AAAAA)-3' and alkylates the N3 position of the 3'-adenine by its CPI left-hand unit present in the molecule (Hurley et al., *Science* (1984) 226:843). Despite its potent and broad antitumor activity, CC-1065 cannot be used in humans because it causes delayed death in experimental animals.

Many CC-1065 analogs have been synthesized. Some of these synthetic analogs are U-73975 (FIG. 1, adozelesin, Aristoff, *Adv. in Med. Chem.* (1993) 2:67); U-77779 (bizelesin, Aristoff (1993)); U-80244 (FIG. 1, carzelesin, Aristoff, (1993)); KW-2189 (Ogasawara et al., *Jpn. J. Cancer Res.* (1994) 85:418); YW-052, YW-053, (FIG. 1, Wang and Lown, *Book of Abstracts*-209th Amer. Chem. Soc. National Meeting (1995)); CBI-CDPI$_1$ and CBI-CDPI$_2$ (Boger and Johnson, *Proc. Natl. Acad. Sci. U.S.A.* (1995) 92:3642). U-73975, U-77779 and U-80244 are in clinical trials in the USA (Aristoff, 1993) and KW 2189 is in clinical trials in Japan (Niitani et al., *Proceeding. Amer. Asso. Cancer Res.* (1995) 243). The monoclonal antibody conjugate, DC1 (FIG. 3, Chari, R. V. J., et al., *Cancer Res.*, (1995) 55:4079) has recently been reported.

Another class of related compounds includes netropsin (Julia, M., et al., *Acad. Sci.* (1963) 257:1115) and distamycin (Arcamone, F. M., et al., *Gazz. Chim. Ital.* (1967) 97:1097). Their structures are shown in FIG. 2. Both compounds are positively charged. These compounds are not used as antitumor agents because of their low therapeutic efficacy. A synthetic analog of this class of compound, FCE 24517 (FIG. 2, Arcamone, F. M., et al., *J. Med. Chem.* (1989) 32:774), was reported. FCE 24517 is a conjugate of benzoic acid nitrogen mustard and oligopyrrole, and is currently undergoing clinical trials.

A limitation of currently used antitumor drugs is the lack of selectivity to cancerous cells over normal tissue. It would be desirable to provide high potency compounds which were selective for cancerous cells over normal tissue. It would also be useful to provide labelling agents which selectively label DNA. This invention fulfills these and related needs.

SUMMARY OF THE INVENTION

The present invention provides compounds of the formula:

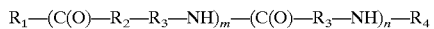

wherein:

$R_1$ is selected from the group consisting of:

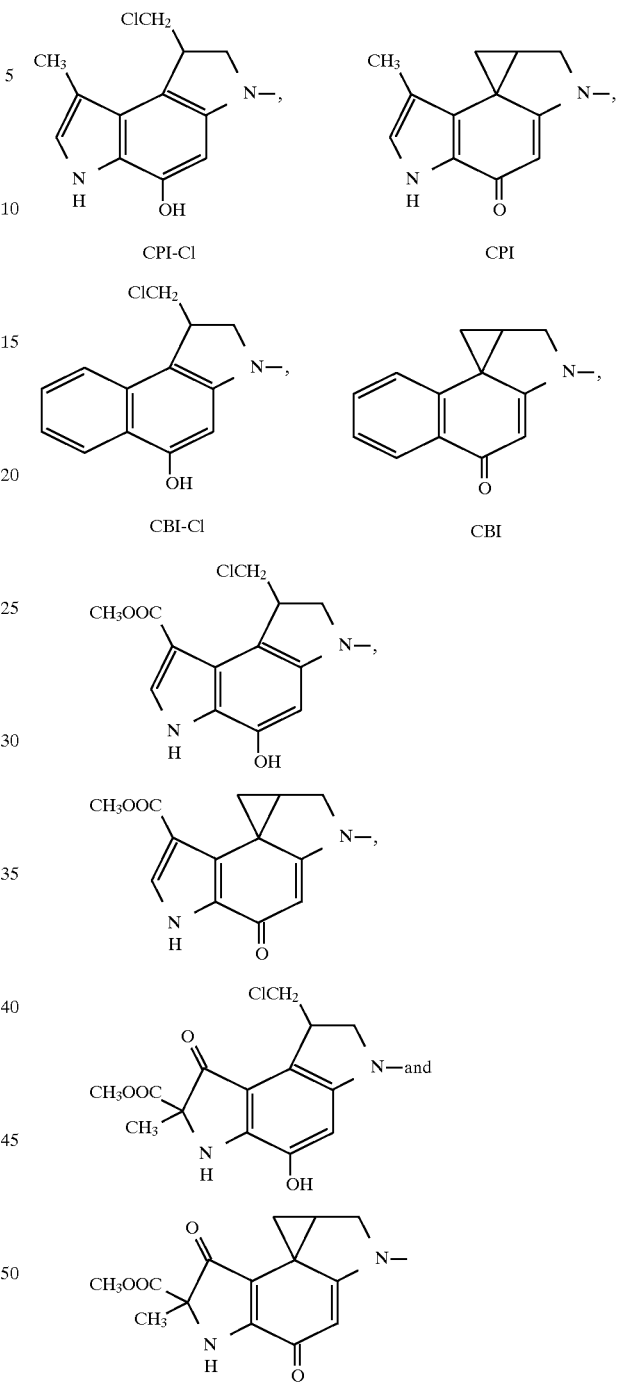

wherein:
  each $R_2$ is the same or different and is a valence bond or a divalent hydrocarbyl radical;
  each $R_3$ is the same or different and is a divalent monocyclic or bicyclic heterocyclic aromatic radical;
  m and n are integers from 0 to 3, where m+n≦3; and
  $R_4$ is independently:
    H; $C_1$–$C_6$ alkyl; $C_1$–$C_6$ hydroxyalkyl; $C_1$–$C_6$ hydroxycycloalkyl; hydroxyphenyl; hydroxymethylphenyl; hydroxybenzyl; $C_1$–$C_6$ aminoalkyl; $C_1$–$C_6$ alkylamino$C_1$–$C_6$ alkyl; di-($C_1$–$C_6$)-alkylamino$C_1$–$C_6$ alkyl; $C_1$–$C_6$ ureidoalkyl; an alkyl group carrying a positively charged substituent; Z where Z is either X or Y, where X is a structure of the Formula I,

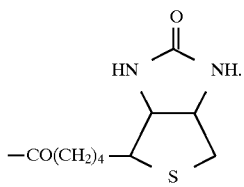

(Formula I)

and Y is a structure of the Formula II,

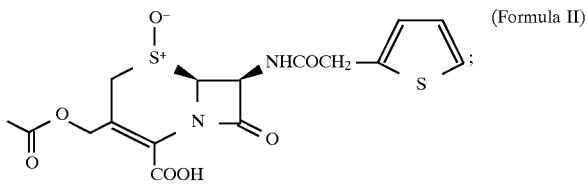

(Formula II)

or $C(O)R_5$, where $R_5$ is independently:
$NH_2$; $C_1$–$C_6$ alkyl; $C_1$–$C_6$ hydroxyalkyl; $C_1$–$C_6$ hydroxycycloalkyl; hydroxyphenyl; hydroxymethylphenyl; hydroxybenzyl; $C_1$–$C_6$ aminoalkyl; $C_1$–$C_6$ alkylamino$C_1$–$C_6$alkyl; di-($C_1$–$C_6$)-alkylamino$C_1$–$C_6$alkyl; $C_1$–$C_6$ ureidoalkyl; a $C_1$–$C_6$ alkyl group carrying a positively charged substituent; $C_1$–$C_6$ alkyl-NHZ; $C_1$–$C_6$ cycloalkyl-NHZ; phenyl-NHZ; —$CH_2$-phenyl-NHZ; -phenyl-$CH_2$—NHZ; L-S where L is a linking group and S is a substrate for an enzyme; $C_1$–$C_6$ alkyl-$OR_6$; $C_1$–$C_6$ cycloalkyl-$OR_6$; phenyl-$OR_6$; —$CH_2$-phenyl-$OR_6$; or -phenyl-$CH_2$—$OR_6$, where $R_6$ is selected from the group consisting of:

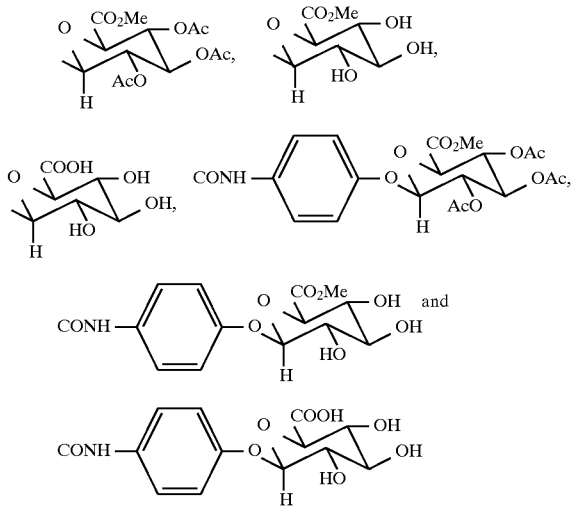

provided that, when $R_4$ is H or $C_1$–$C_6$ alkyl or when $R_5$ is $NH_2$, $C_1$–$C_6$ alkyl or $C_1$–$C_6$ aminoalkyl, $R_1$ is not CPI or CPI-Cl when one or more of the $R_3$'s is pyrrole or imidazole; provided that, when $R_4$ is H or $C_1$–$C_6$ alkyl or when $R_5$ is $NH_2$ or $C_1$–$C_6$ alkyl:
(1) $R_1$ is not CPI or CPI-Cl when m+n=1 and $R_3$ is quinoline or indole; or
(2) $R_1$ is not CBI or CBI-Cl or CPI or CPI-Cl when m+n=2 and both $R_3$'s are indole; provided that, when $R_4$ is H or $C_1$–$C_6$ alkyl:

(1) $R_1$ is not CBI or CBI-Cl when m+n=1 and $R_3$ is indole; or
(2) $R_1$ is not CPI or CPI-Cl when m+n=2 and one of the $R_3$'s is indole or benzofuran.

The invention also provides prodrugs related to the above compounds, in particular prodrugs in which the compounds are linked to enzyme substrates and antibodies. The invention also provides methods of inhibiting tumor growth using the compounds disclosed herein. In addition, the compounds and their derivatives disclosed herein are useful in alkylating and labelling DNA, thus facilitating the detection, purification and isolation of DNA.

DESCRIPTION OF THE PREFERRED EMBODIMENT

Figure 1:
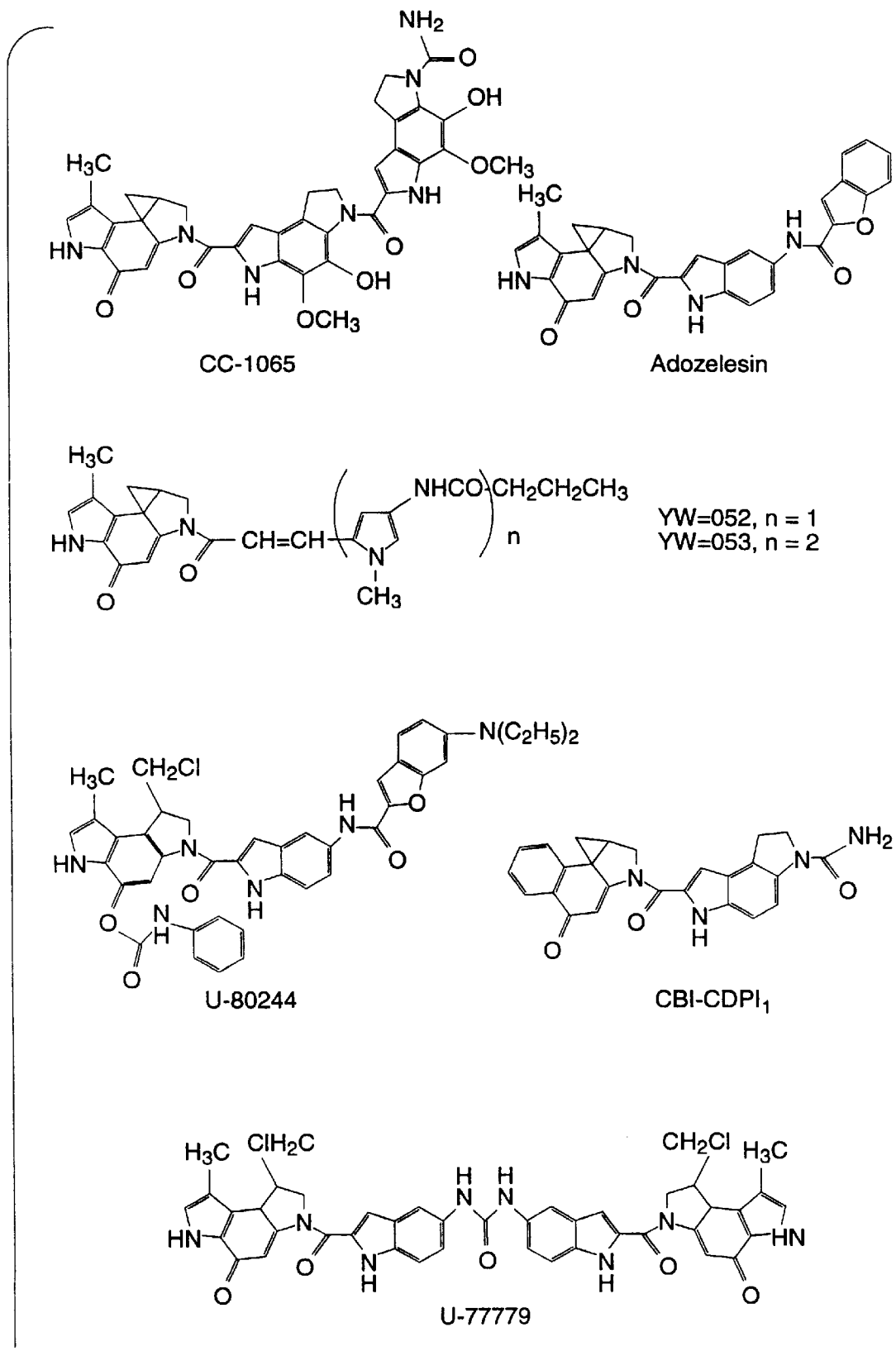
FIG. 1 shows structures of CC-1065, adozelesin, YW-052, YW-053, U-80244, CBI-$CDPI_1$, CBI-$CDPI_2$, KW-2189, and U-77779.
Figure 1:
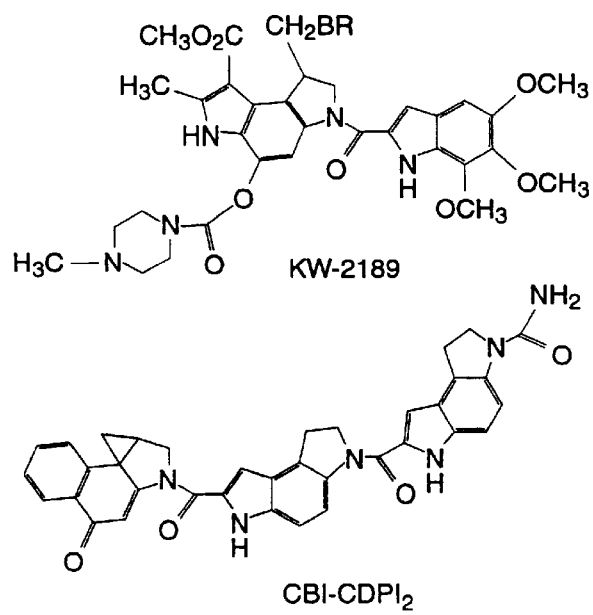
Figure 2:
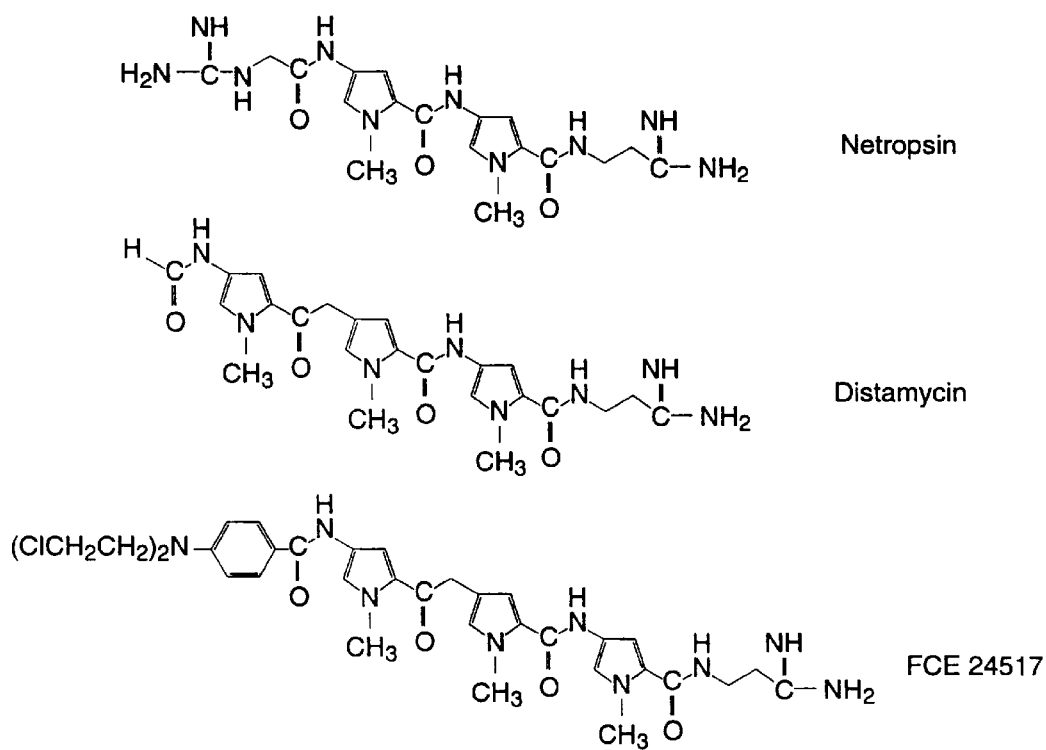
FIG. 2 shows structures of netropsin, distamycin and FCE 24517.
Figure 3:
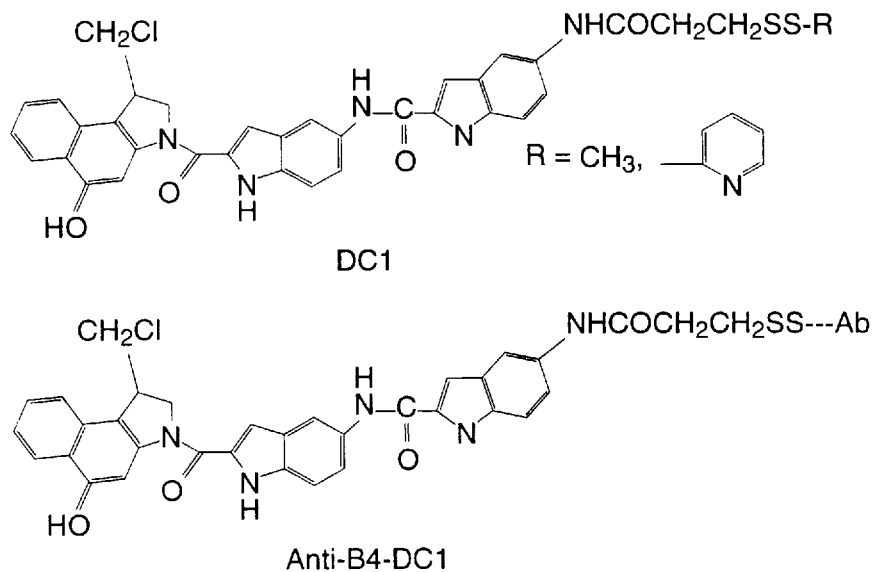
FIG. 3 shows structures of DC1 and its monoclonal antibody conjugate.

The following definitions are set forth to illustrate and define the meaning and scope of the various terms used to describe the invention herein.

The term "hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "alkyl" refers to a branched or straight chain acyclic, monovalent saturated hydrocarbon radical of one to twenty carbon atoms.

The term "lower-alkyl" refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "alkenyl" refers to an unsaturated hydrocarbon radical which contains at least one carbon—carbon double bond and includes straight chain, branched chain and cyclic radicals.

The term "alkynyl" refers to an unsaturated hydrocarbon radical which contains at least one carbon—carbon triple bond and includes straight chain, branched chain and cyclic radicals.

The term "lower" referred to herein in connection with organic radicals or compounds respectively defines such with up to and including six, preferably up to and including four carbon atoms. Such groups may be straight chain or branched.

The term "aryl" refers to an aromatic carbocyclic radical having a single ring (e.g., phenyl) or multiple condensed rings (e.g., naphthyl).

The term "heterocyclic aromatic" refers to an aromatic mono- or poly-cyclic radical having at least one heteroatom within a ring, e.g., nitrogen, oxygen or sulfur. For example, typical heteroaryl groups with one or more nitrogen atoms are tetrazoyl, pyrrolyl, pyridyl (e.g., 4-pyridyl, 3-pyridyl, 2-pyridyl), pyridazinyl, indolyl, quinolyl (e.g., 2-quinolyl, 3-quinolyl etc.), imidazolyl, isoquinolyl, pyrazolyl, pyrazinyl, pyrimidinyl, pyridonyl or pyridazinonyl; typical oxygen heteroaryl radicals with an oxygen atom are 2-furyl, 3-furyl or benzofuranyl; typical sulfur heteroaryl radicals are thienyl, and benzothienyl; typical mixed heteroatom heteroaryl radicals are furazanyl, oxazolyl, isoxazolyl, thiazolyl, and phenothiazinyl. Further the term also includes instances where a heteroatom within the ring has been oxidized, such as, for example, to form an N-oxide or sulfone.

The term "ureido" refers to the group —NH—C(O)—NH$_2$.

The term "linker" refers to any chemically and biologically compatible covalent grouping of atoms which can serve to link the compounds of this invention to antibodies or enzyme substrates. Generally, preferred linking groups have from 0–20 carbons, preferably 0–8 carbons, more preferably 0–3 carbons and/or 0–10 heteroatoms (NH, O, S, P etc.) and may be branched or straight chain or contain rings. The linkage can be designed to be hydrophobic or hydrophilic. The linking group can contain single and/or double bonds and saturated or aromatic rings. The linking group may contain groupings such as amide, ester, phosphate, ether, sulfide, disulfide, amine and the like.

The representation "ω-substituent alkyl" means that the substituent is on the distal (i.e., terminal) carbon of the alkyl chain.

The present invention includes synthesis, biological evaluation and therapeutic use of novel DNA alkylating agents and their prodrugs. The free drugs, which do not need enzyme activation, have potent antitumor activities in vitro against U937 leukemia cells and B16 melanoma cells (Tables 1–2).

TABLE 1

Cytotoxicity of Invented Compounds Against U937 Cells

| Compound | IC$_{50}$ (nM) |
|---|---|
| Doxorubicin | 100 |
| YW-161 | 5 |
| YW-198 | 0.2 |
| YW-200 | 0.01 |
| YW-201 | 0.07 |
| YW-202 | 0.2 |
| YW-210 | 0.3 |
| YW-212 | 0.05 |
| YW-213 | 0.2 |

TABLE 1-continued

Cytotoxicity of Invented Compounds Against U937 Cells

| Compound | IC$_{50}$ (nM) |
|---|---|
| YW-214 | 0.6 |
| YW-215 | 0.09 |
| YW-216 | 0.09 |
| YW-222 | 0.5 |
| YW-231 | 0.6 |
| YW-235 | 0.7 |
| YW-242 | 0.09 |
| YW-247 | 1.4 |
| YW-249 | 0.55 |
| YW-254 | 0.1 |
| YW-258 | 0.08 |
| YW-259 | 0.09 |
| YW-284 | 9 |
| YW-285 | 0.9 |
| YW-286 | 5.5 |

TABLE 2

Cytotoxicity of Invented Compounds Against B16 Melanoma

| Compound | IC$_{50}$ (nM) |
|---|---|
| Doxorubicin | 780 |
| YW-200 | 7.2 |
| YW-231 | 4.0 |
| YW-242 | 11.0 |

They are also effective against tumor cells in mice with life-span increase of up to 91%. These compounds shows no sign of delayed death that has limited the clinic use of the natural product CC-1065. Other CC-1065 analogs, U-73975, U-77779, U-80244 and KW 2189, which do not cause delayed death are currently under clinical trials.

One advantage of some of these new compounds is that the hydroxy or amino group on the side chain enhances water solubility. This is an important feature because poor water solubility often causes difficulties in formulation, administration of antitumor agents, and sometimes side effects.

Another advantage of these compounds is that an amide bond at the end of the heterocycle side chain or a double bond connecting the DNA alkylating moiety and the heterocycle side chain increases DNA-binding abilities of these molecules which then increase their antitumor activity. The improved water solubility and increased DNA-binding ability enhances the antitumor activity of these compounds.

Unlike CC-1065, these new compounds are composed of different heterocycles. CC-1065 binds to AT-rich sequences of the DNA. While these new compounds will bind to AT-rich sequences of DNA, they will also bind to other sequences of DNA such as CG or mixed AT and CG sequences of DNA. Thus, the compounds are able to bind to and label DNA.

Compounds of this invention are of the general formula:

wherein:

$R_1$ is selected from the group consisting of:

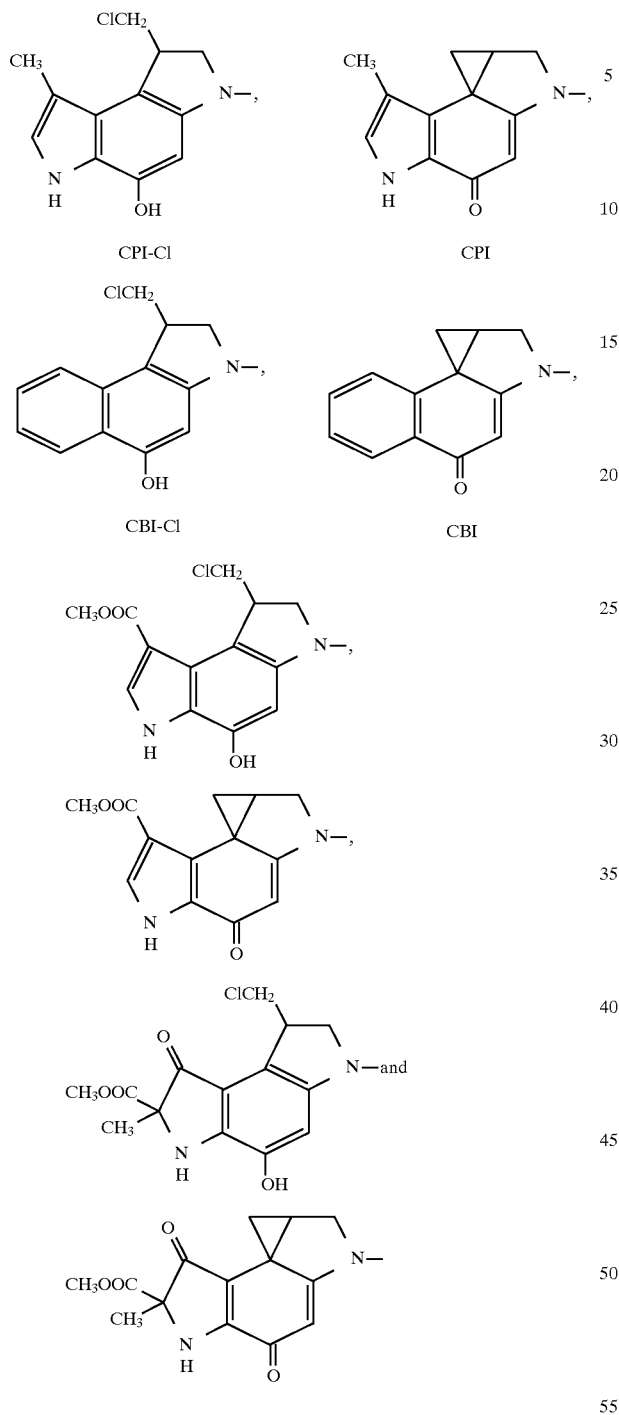

wherein:
  each $R_2$ is the same or different and is a valence bond or a divalent hydrocarbyl radical;
  each $R_3$ is the same or different and is a divalent monocyclic or bicyclic heterocyclic aromatic radical;
  m and n are integers from 0 to 3, where $m+n \leq 3$; and $R_4$ is independently:
  H; $C_1$–$C_6$ alkyl; $C_1$–$C_6$ hydroxyalkyl; $C_1$–$C_6$ hydroxycycloalkyl; hydroxyphenyl; hydroxymethylphenyl; hydroxybenzyl; $C_1$–$C_6$ aminoalkyl; $C_1$–$C_6$ alkylamino$C_1$–$C_6$alkyl; di-($C_1$–$C_6$)-alkylamino$C_1$–$C_6$ alkyl; $C_1$–$C_6$ ureidoalkyl; an alkyl group carrying a positively charged substituent; Z where Z is either X or Y, where X is a structure of the Formula I,

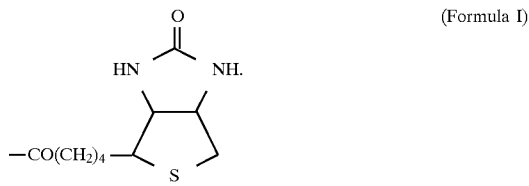

and Y is a structure of the Formula II,

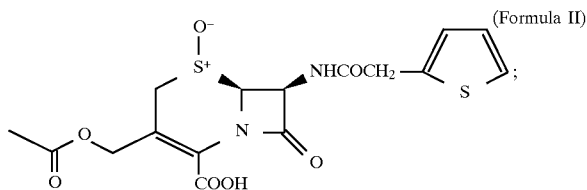

or $C(O)R_5$, where $R_5$ is independently:
  $NH_2$; $C_1$–$C_6$ alkyl; $C_1$–$C_6$ hydroxyalkyl; $C_1$–$C_6$ hydroxycycloalkyl; hydroxyphenyl; hydroxymethylphenyl; hydroxybenzyl; $C_1$–$C_6$ aminoalkyl; $C_1$–$C_6$ alkylamino$C_1$–$C_6$ alkyl; di-($C_1$–$C_6$)-alkylamino$C_1$–$C_6$ alkyl; $C_1$–$C_6$ ureidoalkyl; a $C_1$–$C_6$ alkyl group carrying a positively charged substituent; $C_1$–$C_6$ alkyl-NHZ; $C_1$–$C_6$ cycloalkyl-NHZ; phenyl-NHZ; —$CH_2$-phenyl-NHZ;-phenyl-$CH_2$—NHZ; L-S where L is a linking group and S is a substrate for an enzyme; $C_1$–$C_6$ alkyl-$OR_6$; $C_1$–$C_6$ cycloalkyl-$OR_6$; phenyl-$OR_6$; —$CH_2$-phenyl-$OR_6$; or -phenyl-$CH_2$—$OR_6$, where $R_6$ is selected from the group consisting of:

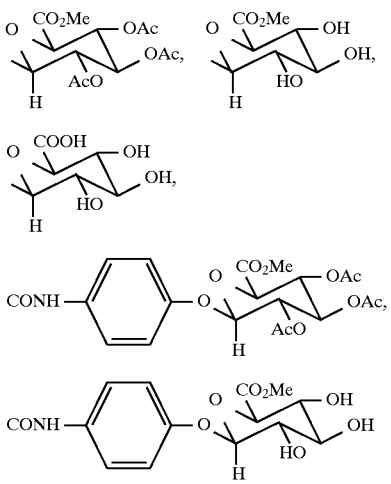

and

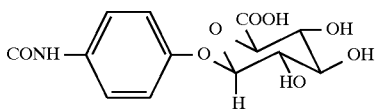

provided that, when $R_4$ is H or $C_1$–$C_6$ alkyl or when $R_5$ is $NH_2$, $C_1$–$C_6$ alkyl or $C_1$–$C_6$ aminoalkyl, $R_1$ is not CPI or CPI-Cl when one or more of the $R_3$'s is pyrrole or imidazole; provided that, when $R_4$ is H or $C_1$–$C_6$ alkyl or when $R_5$ is $NH_2$ or $C_1$–$C_6$ alkyl:
(1) $R_1$ is not CPI or CPI-Cl when m+n=1 and $R_3$ is quinoline or indole; or (2) R$_1$ is not CBI or CBI-Cl or CPI or CPI-Cl when m+n=2 and both R$_3$'s are indole;
provided that, when R$_4$ is H or C$_1$–C$_6$ alkyl:
(1) R$_1$ is not CBI or CBI-Cl when m+n=1 and R$_3$ is indole; or
(2) R$_1$ is not CPI or CPI-Cl when m+n=2 and one of the R$_3$'s is indole or benzofuran.

Representative alkyl groups include but are not limited to CH$_3$, CH$_3$CH$_2$—, CH$_3$CH$_2$CH$_2$—, CH$_3$CH(CH$_3$)—, CH$_3$CH$_2$CH$_2$CH$_2$—, CH$_3$CH(CH$_3$)CH$_2$— and CH$_3$CH$_3$CH(CH$_3$)CH$_2$—.

Representative hydroxyalkyl groups include, but are not limited to —CH$_2$OH, —CH$_2$CH$_2$OH, —CH$_2$CH$_2$CH$_2$OH, —CH$_2$CH(CH$_3$)OH, —CH$_2$CH$_2$CH$_2$CH$_2$OH, —CH$_2$CH(CH$_3$)CH$_2$OH, —CH$_2$CH$_2$CH(CH$_3$)CH$_2$OH, —C$_6$H$_{10}$OH, C$_6$H$_4$OH— and CH$_2$C$_6$H$_4$OH.

Representative aminoalkyl groups include, but are not limited to —CH$_2$NH$_2$, —CH$_2$CH$_2$NH$_2$, —CH$_2$CH$_2$CH$_2$NH$_2$, —CH$_2$CH(CH$_3$)NH$_2$, —CH$_2$CH$_2$CH$_2$CH$_2$NH$_2$, —CH$_2$CH(CH$_3$)CH$_2$NH$_2$, —CH$_2$CH$_3$CH(CH$_3$)CH$_2$NH$_2$, —C$_6$H$_{10}$NH$_2$, —C$_6$H$_4$NH$_2$ and —CH$_2$C$_6$H$_4$NH$_2$.

This invention provides monoclonal antibody conjugates and enzyme substrate conjugates of novel highly potent compounds. These conjugates are used to inhibit and prevent tumor growth using monoclonal antibody-directed enzyme prodrug therapy (ADEPT, Bagshawe, Br. *J. Cancer* 1989, 60:272) or antibody-directed catalysis (ADC, Jungheim and Shepped, *Chem. Rev.* 1994, 94:1553). In these approaches, an enzyme is conjugated to a tumor specific antibody. The antibody selectively localizes the enzyme on the tumor cell surface. Subsequent administration of a prodrug which is a substrate of the enzyme results in the enzyme-catalyzed release of the free drug at the tumor site. This strategy addresses the stoichiometry, controlled drug release and poor antibody penetration problems associated with the use of antibody-drug conjugate alone. In addition, because the process of drug release is enzymatic, a large amount of free drug can be generated by a single enzyme.

The drugs used herein are high potency compounds. Thus, small amounts of antibody and drug can be used. Using a low amount of antibody minimizes immunogenic side effects, alleviates formulation problems, increases the likelihood of drug penetration into the desired tissue and reduces overall cost.

Figure 4:
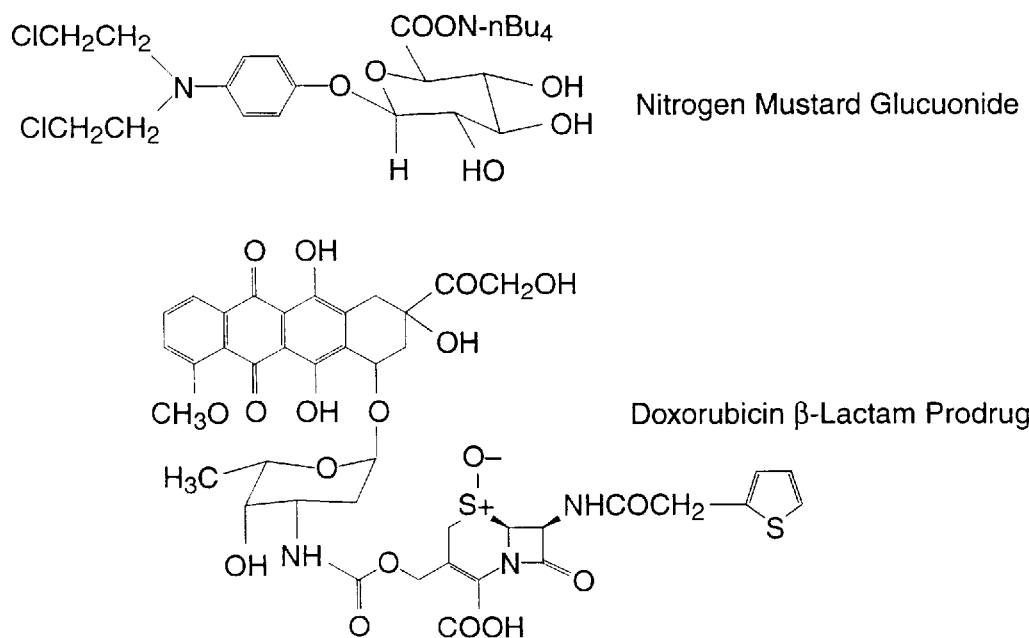
FIG. 4 shows structures of nitrogen mustard glucuronide and doxorubicin β-lactam prodrug.

Two examples related to this invention are shown in FIG. 4. The first example is an ADEPT approach employing the enzyme β-glucuronidase. A nitrogen mustard glucuronide was activated by β-glucuronidase or β-glucuronidase-antibody conjugate to generate phenol mustard which is more toxic to cells than the parent compound (Wang, S. M., et al., *Cancer Res.*, 1992, 52:4484). The second example uses β-lactamase to cleave the doxorubicin from its B-lactam prodrug (Jungheim, L. N., et al., *Heterocycles*, 1993, 35:339).

The new DNA alkylating agents invented here are among the most potent antitumor agents ever reported. The prodrugs in this invention are the first example using these highly potent molecules in an ADEPT approach. This kind of prodrug has several advantages. First very little drug is needed. Second, since minimal amounts of monoclonal antibody-enzyme conjugate are needed, problems due to immunogenicity are reduced.

Figure 5:
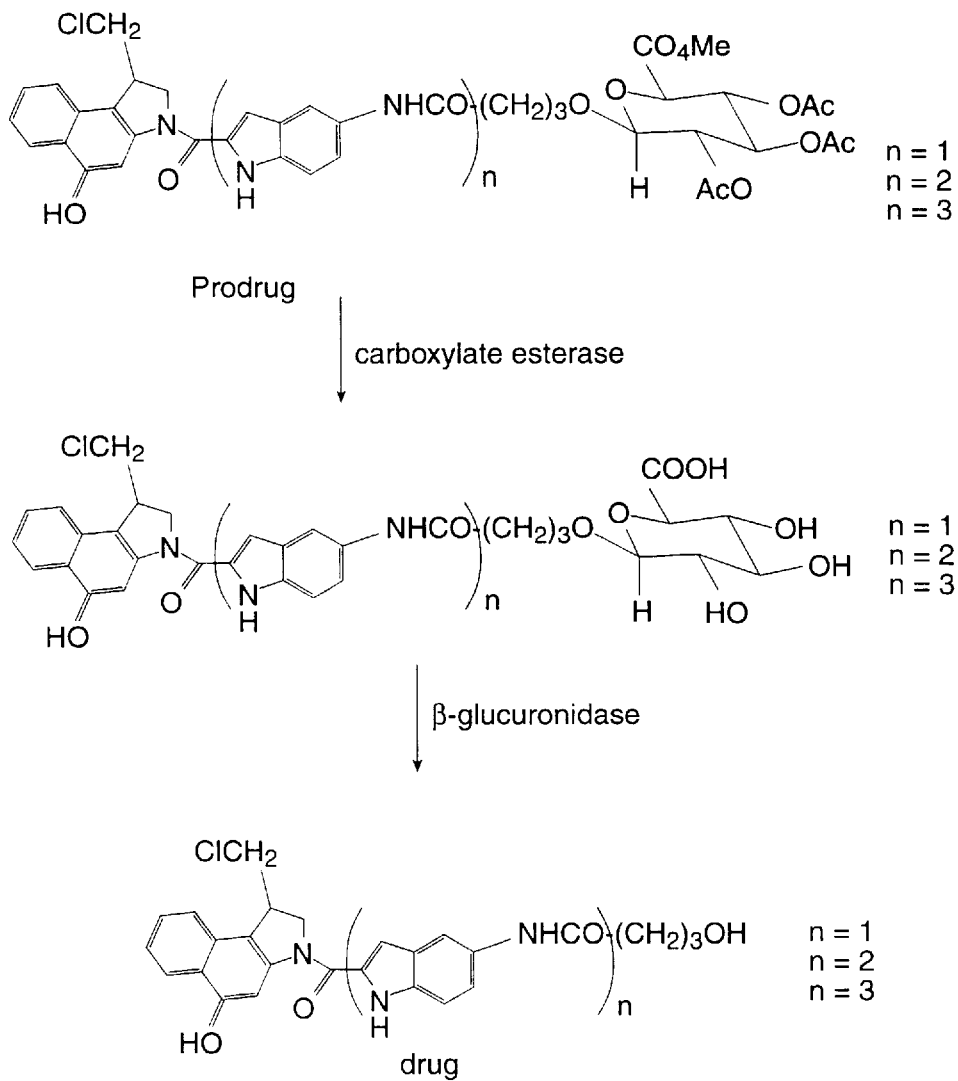
FIG. 5 shows the mechanism of activation of glucuronide prodrugs.
Figure 6:
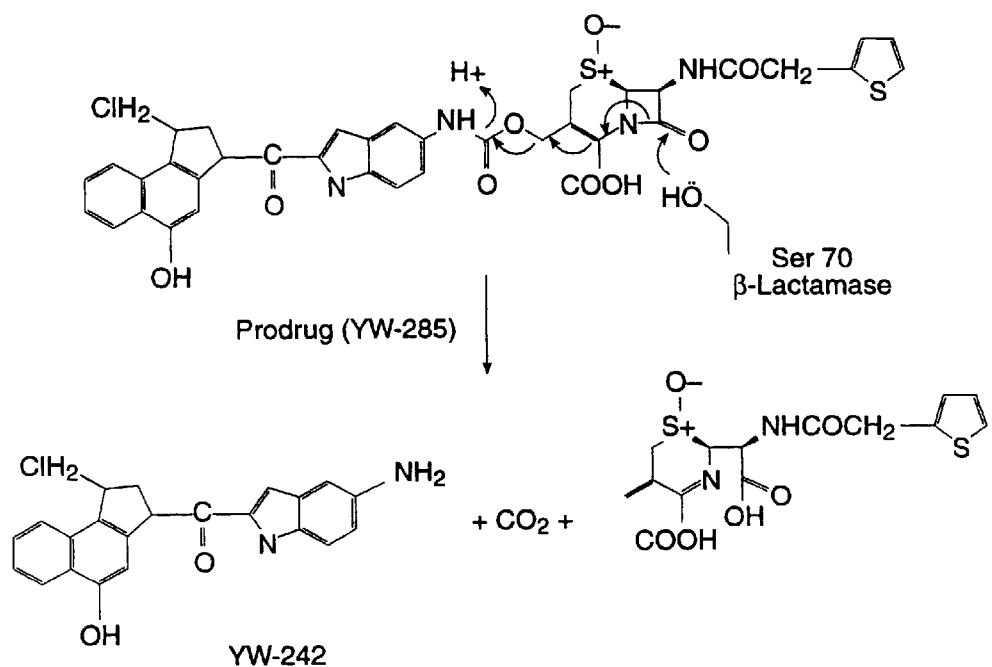
FIG. 6 shows the mechanism of activation of β-lactam prodrugs.

All of the prodrugs contained in this invention are less toxic than their corresponding free drugs. In the presence of related enzymes or monoclonal antibody-enzyme conjugates such as glucuronidase or β-lactamase these prodrugs will be activated to release the free drugs (FIGS. 5 and 6).

Using such potent molecules for monoclonal antibody-drug conjugate has advantages over using low potency agents. The tumor specific antibody will carry these molecules specifically to tumor cells, thus enhancing the therapeutic efficacy of these compounds. The monoclonal antibody-drug conjugates are still very toxic to cancer cells. The Mab-YW-242 conjugates were tested in vitro against human liver cancer HepG2 cells. IC$_{50}$ values for cell proliferation were determined by incorporation of $^3$H-thymidine. The results are shown in Table 3.

TABLE 3

| | IC$_{50}$ Values of the Mab-drug Conjugate (mM) | | |
|---|---|---|---|
| Cell | YW-242 | Mab-YW-242 | Doxorubicin |
| HepG2 | 0.2 | 0.5 | 6 |

Generally, the enzyme substrate or antibody is attached to a DNA alkylating agent of this invention by means of a bifunctional linker. "Linking group" shall mean the "chemical arm" between the enzyme substrate and the antibody and the DNA alkylating agent. As one skilled in the art will recognize, to accomplish the requisite chemical structure, each of the reactants must contain the necessary reactive groups.

Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the enzyme substrate and the antibody. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon—carbon bonds are acceptable examples of chemically compatible linking groups. Other chemically compatible compounds which may comprise the linking group are set forth in U.S. Pat. Nos. 5,470,997 (col. 2 and col. 4–7); 5,470,843 (cols. 11–13); and 5,470,932.

Repesentative spacers which can be used to attach an enzyme substrate by acylation or alkylation of the terminal oxygen or nitrogen atom include the following: —CH$_2$OH, —CH$_2$CH$_2$OH, —CH$_2$CH$_2$CH$_2$OH, —CH$_2$CH(CH$_3$)OH, —CH$_2$CH$_2$CH$_2$CH$_2$OH, —CH$_2$CH(CH$_3$)CH$_2$OH, —CH$_2$CH$_3$CH(CH$_3$)CH$_2$OH, —C$_6$H$_{10}$OH, —C$_6$H$_4$OH and —CH$_2$C$_6$H$_4$OH; and —CH$_2$NH$_2$, —CH$_2$CH$_2$NH$_2$, —CH$_2$CH$_2$CH$_2$NH$_2$, —CH$_2$CH(CH$_3$)NH$_2$, —CH$_2$CH$_2$CH$_2$CH$_2$NH$_2$, —CH$_2$CH(CH$_3$)CH$_2$NH$_2$, —CH$_2$CH$_3$CH(CH$_3$)CH$_2$NH$_2$, —C$_6$H$_{10}$NH$_2$, —C$_6$H$_4$NH$_2$ and —CH$_2$C$_6$H$_4$NH$_2$.

In addition to glucuronidase and β-lactamase substrates, other substrates which can be linked to a DNA alkylating agent of this invention and their corresponding enzymes include glutamic acid for carboxypeptidase, phosphate (phosphoric acid) for alkaline phosphatase, α-galactose for α-galactosidase and nitrobenzyl carboxylate (—C(O)OCH$_2$C$_6$H$_5$NO2) for nitroreductase.

The compounds of the present invention can be used as antitumor agents. The in vitro and in vivo antitumor activities presented here demonstrate the validity of this statement. They are also of utility in alkylating, labelling, detecting and isolating DNA.

Thus, the novel compounds and conjugates provided by the present invention may be incorporated into aqueous solutions for injection (intravenous, subcutaneous and the like) or intravenous infusion or into ointment preparations for administration via the skin and mucous membranes. The conjugates of this invention are administered at a therapeutically effective dosage, i.e., that amount which, when administered to a mammal in need thereof, is sufficient to effect treatment, as described above (for example, to reduce or otherwise treat the disease, e.g., control or inhibit tumor growth when cancer is being treated. Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about .01% w to 99.99% w excipient. Preferably the drug is present at a level of about 10% w to about 70% w.

Generally, an acceptable daily dose is of about 0.04 μg to 50 mg per kilogram body weight of the recipient per day with lower doses in the range of 0.08 μg –10 μg being preferred. Thus, for administration to a 70 kg person, the dosage range would be about 28 μg to 3.5 g per day. Such use and optimization is well within the ambit of those of ordinary skill in the art. (Fleming, et al., *J. Nat. Cancer Institute*, 1994, 86(5):368).

Administration can be via any accepted systemic or local route, for example, via parenteral, intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. Administration by intravenous or subcutaneous infusion is usually preferred. Most usually, aqueous formulations will be used. The compounds and conjugates are formulated in a non-toxic, inert, pharmaceutically acceptable carrier medium, preferably at a pH of about 3–8, more preferably at a pH of about 6–8. Generally, the aqueous formulation will be compatible with the culture or perfusion medium. The compositions will include a conventional pharmaceutical carrier or excipient and a compound or conjugate of the DNA alkylating agent, and in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose or mannitol, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in REMINGTON'S PHARMACEUTICAL SCIENCES by E. W. Martin (1985).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with the DNA alkylating agent or conjugate thereof. The level of the conjugate in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

A "pharmaceutically acceptable salt" may be any salt derived from an inorganic or organic acid or base. Salts may be derived from acids or bases.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like.

The base addition salts are derived from inorganic bases such as sodium hydroxide, potassium hydroxide, lithium hydroxide, ammonia, calcium hydroxide, magnesium hydroxide and the like. Cations derived from organic bases include those formed from primary, secondary and tertiary amines, such as isopropylamine, diethylamine, trimethylamine, triethylamine, pyridine, cyclohexylamine, ethylene diamine, monoethanolamine, diethanolamine, triethanolamine, and the like.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

As used herein, the term "therapeutically effective amount" refers to that amount of a compound of the invention which, when administered to a mammal in need thereof, is sufficient to effect treatment (as defined above) as an anticancer agent, an antimicrobial agent or a DNA alkylating agent. The amount that constitutes a "therapeutically effective amount" will vary depending on the compound, the condition or disease and its severity, and the mammal to be treated, its weight, age, etc., but may be determined routinely by one of ordinary skill in the art with regard to contemporary knowledge and to this disclosure.

The following examples are presented to describe the preferred embodiments and utilities of the present invention and are not meant to limit the present invention unless otherwise stated in the claims appended hereto.

Figure 7:
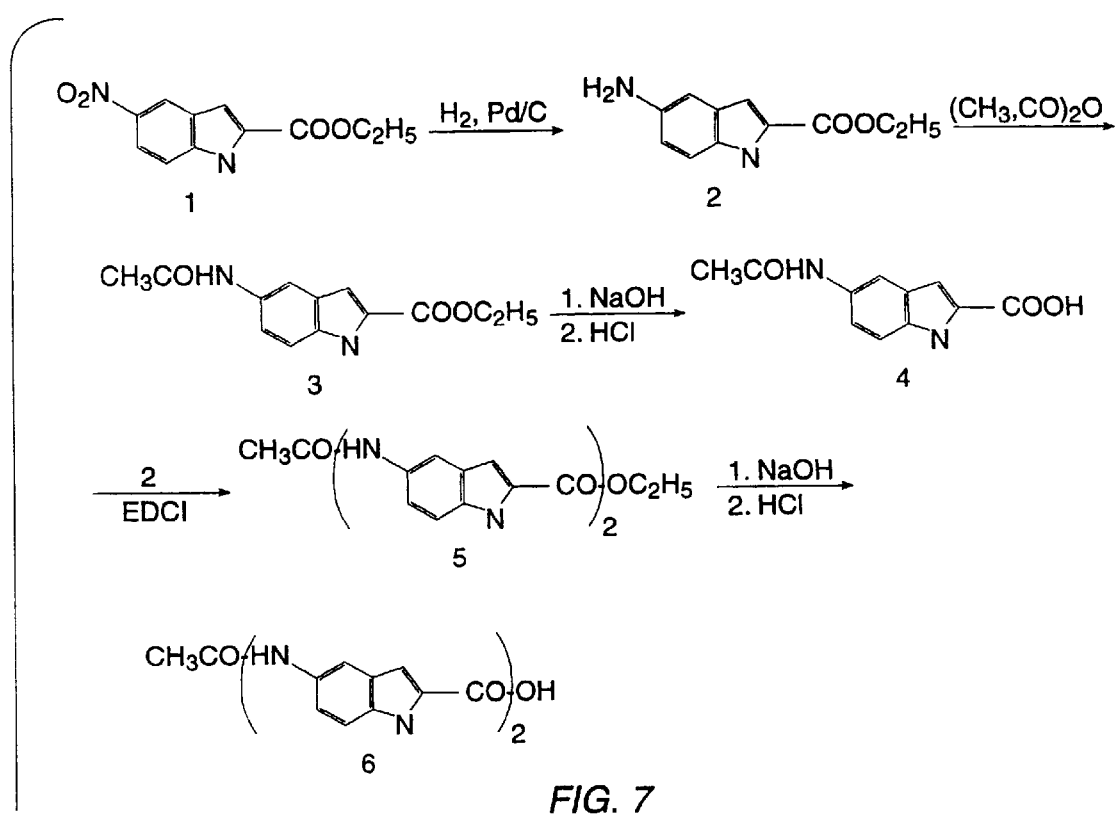
FIG. 7 shows the routes of synthesis of indole derivatives which are used to construct the invented CC-1065 analogs and their prodrugs reported here.
Figure 7:
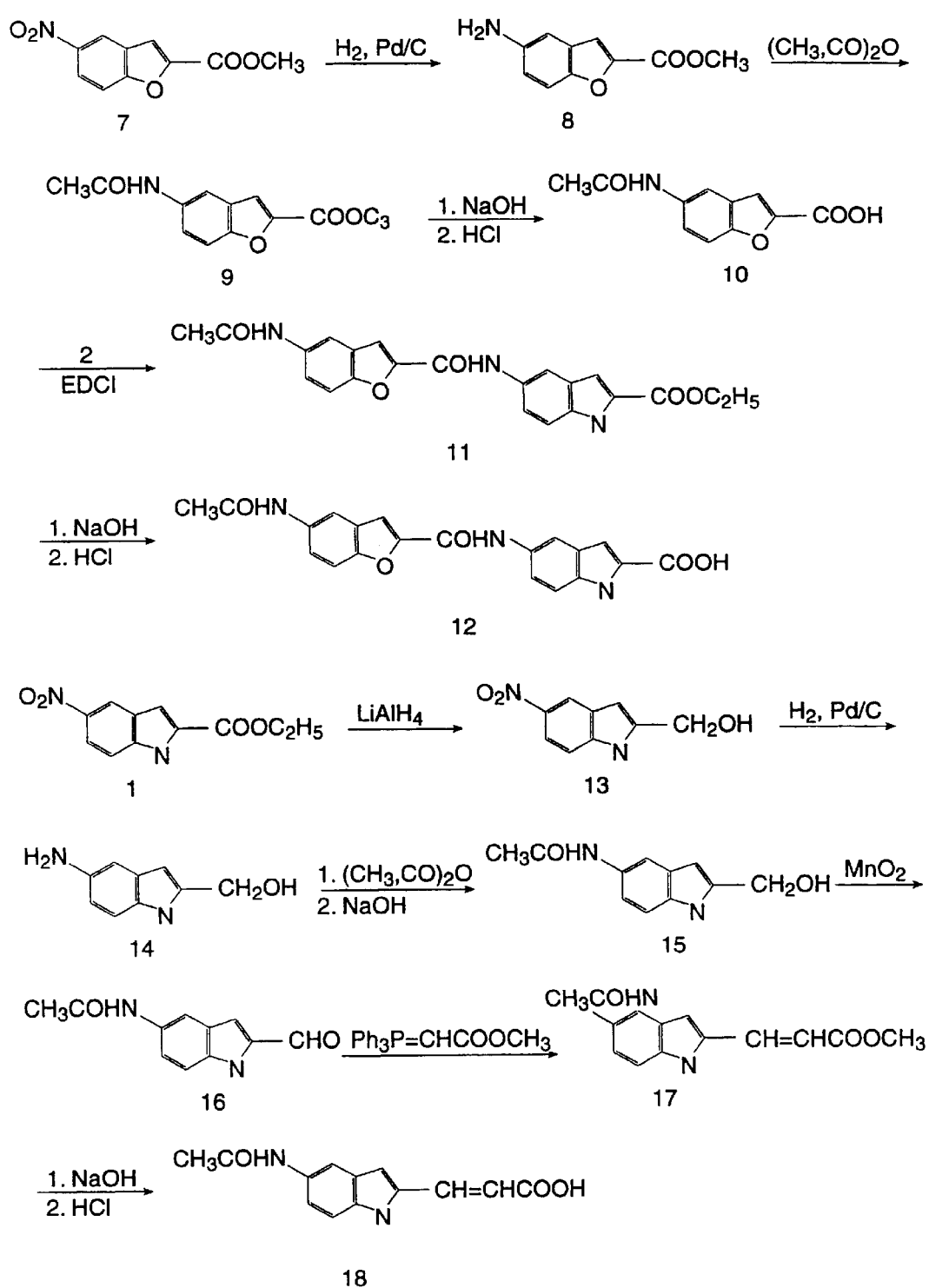
Figure 7:
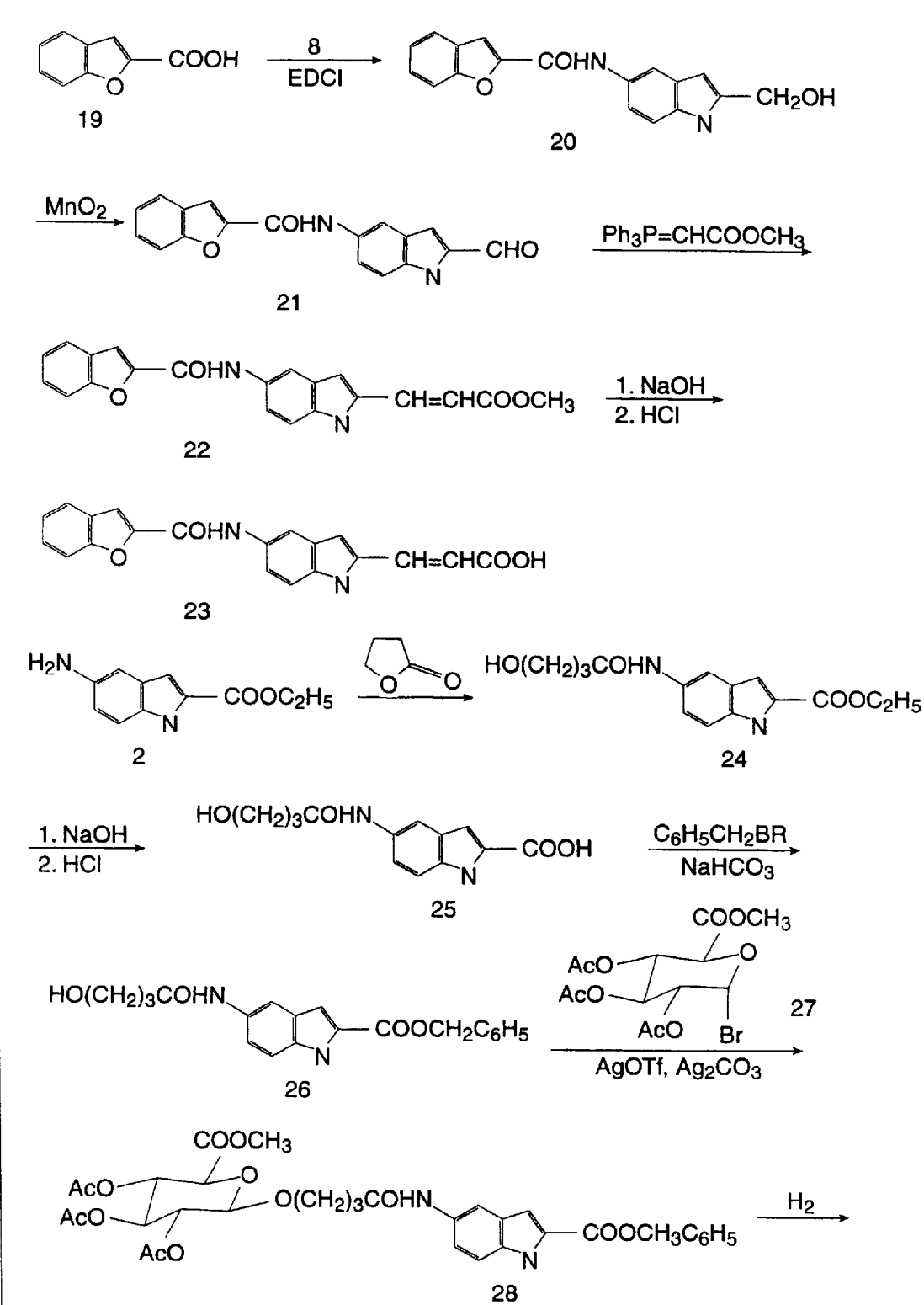
Figure 7:
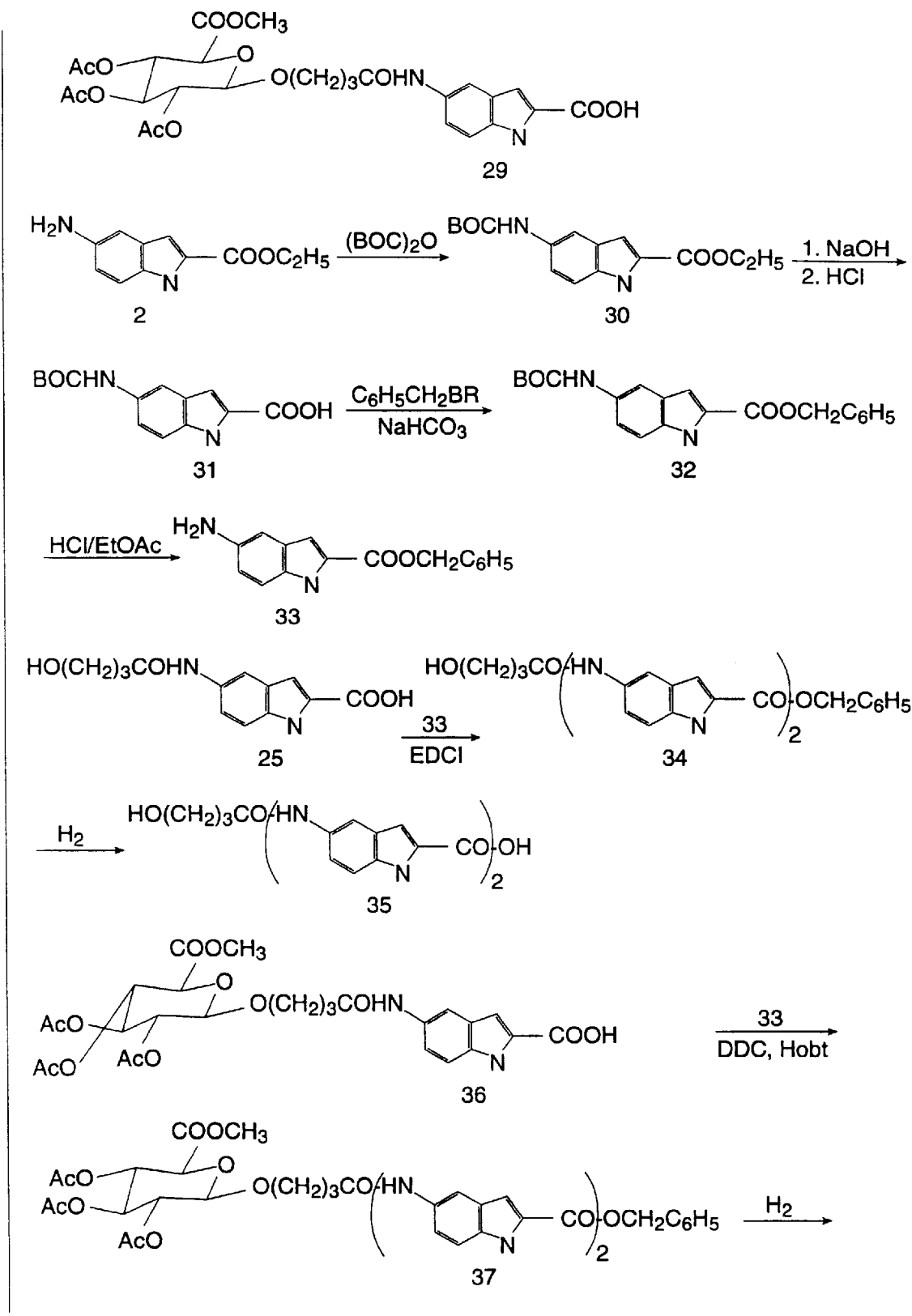
Figure 7:
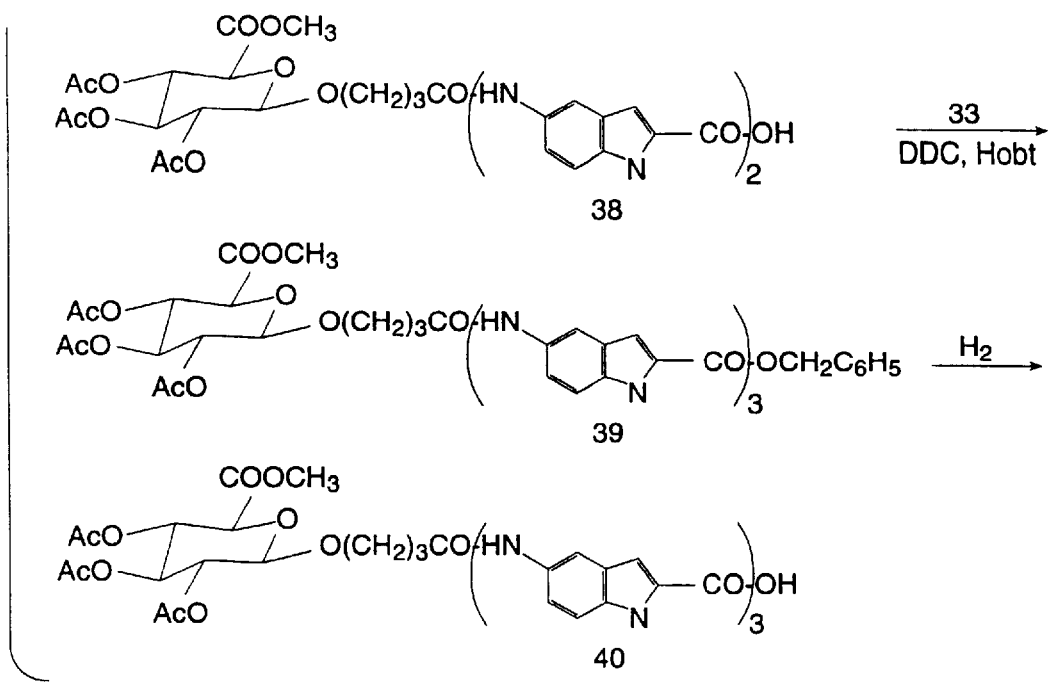
Figure 8:
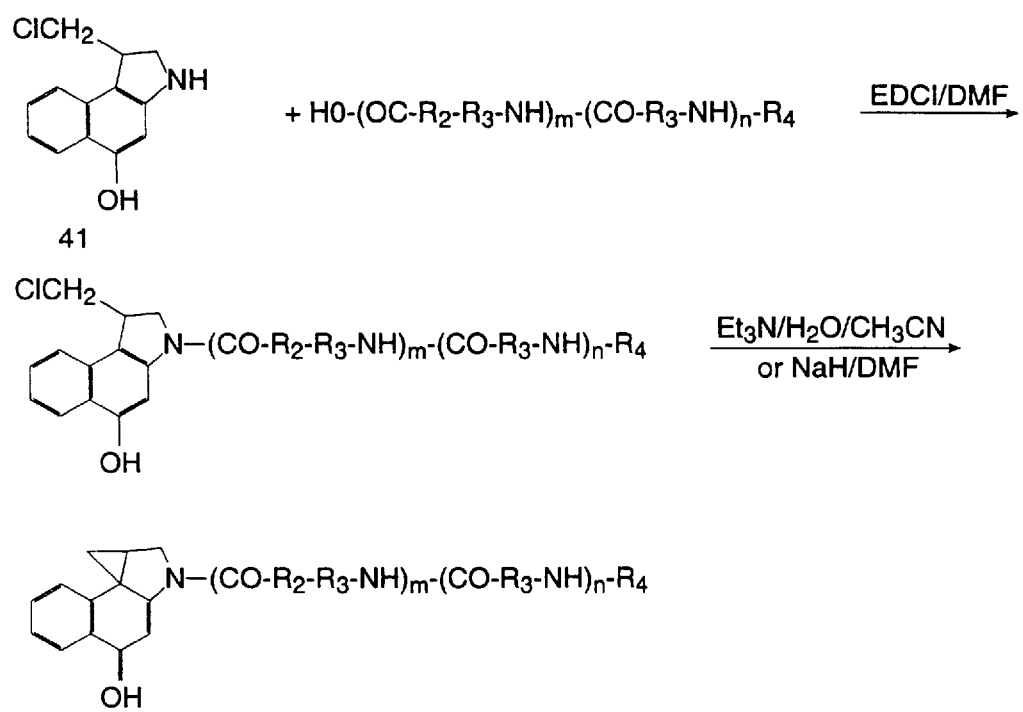
FIG. 8 shows the route of synthesis of CC-1065 analogs and their prodrugs.

The compounds are generally made by linking together R$_2$ and the heterocyclic aromatic groups R$_3$ in the desired order using protecting groups as needed and then attaching the $R_1$ group. In some cases, $R_4$ can behave as a protecting group. Coupling of the various units in the chain is typically accomplished using routine peptide bond forming reactions, e.g., carbodiimide mediated coupling conditions, known to those of skill in the art. Additional protecting groups other than those used herein can be found in *Protective Groups in Organic Synthesis*, 2nd ed. (John Wiley and Sons, Inc., New York, N.Y., 1991). Exemplary synthetic sequences are shown in FIGS. 7 and 8.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures, referred to hereinafter as "conventional means". Specific illustrations of suitable separation and isolation procedures can be had by reference to the examples hereinbelow. However, other equivalent separation or isolation procedures can also be used.

The starting materials and reagents used in preparing the compounds of this invention are either available from commercial suppliers such as Aldrich Chemical Co. or are prepared by methods known to those skilled in the art following procedures set forth in references such as, "Fieser and Fieser's Reagents for Organic Synthesis", Volumes 1–15, John Wiley and Sons, 1991; "Rodd's Chemistry of Carbon Compounds", Volumes 1–5 and Supplementals, Elsevier Science Publishers, 1989; "Organic Reactions", Volumes 1–40, John Wiley and Sons, 1991 and "Comprehensive Heterocyclic Chemistry", Volumes 1–8 by Katritzki and Rees, Pergamon Press, 1984.

Example 1

Synthesis of Indole Derivatives (FIG. 7)

Ethyl 5-acetaminoindole-2-carboxylate (3).

Ethyl 5-nitroindole-2-carboxylate (1, 1 g, 4.27 mmol) was dissolved in ethyl acetate (100 mL) and 5% Pd/C (100 mg) was added. The reaction mixture was hydrogenated for 1 h at room temperature at a pressure of 60 lb/inch$^2$. The reaction mixture was filtered and the solvent was removed in vacuo. A grey powder of 2 was obtained and was used without further purification. A solution of acetyl chloride (174 mL, 2.44 mmol) in dichloromethane (5 mL) was added to a solution of 2 (0.417 g, 2.04 mmol) in DMF (2 mL), dichloromethane (5 mL) and triethylamine (339 mL, 2.44 mmol) dropwise at 0° C. under $N_2$. The reaction mixture was allowed to warm up to room temperature and stirred for 2 h. Water (30 mL) was added and the mixture was extracted with ethyl acetate (40 mL×2). The solution was dried using sodium sulfate and solvent was removed in vacuo. A grey powder 3 was obtained (437 mg, 87% yield). An analytical sample was recrystallized in ethyl acetate. mp: 202°–203° C. $^1$H NMR (DMSO-d6, ppm): 11.74 (s, 1 H, NH), 9.78 (s, 1 h, NH), 7.99 (s, 1 H, Ar—H), 7.38–7.30 (m, 2 H, Ar—H), 7.09–7.08 (m, 1 H, Ar—H), 4.36–4.30 (q, 2 H, J=7.0, 13.7 Hz, $CH_2CH_3$). 2.03 (s, 3 H, $CH_3CO$), 1.36–1.31 (t, 3 H, J=7.0 Hz, $CH_2CH_3$). Anal. ($C_{13}H_{14}N_2O_3$), C, H, N.

5-Acetaminoindole-2-carboxylic acid (4).

3N NaOH (2 mL) was added to a solution of 3 (250 mg, 1.02 mmol) in methanol (7 mL) and the reaction mixture was stirred overnight at room temperature. The reaction mixture was evaporated and water (5 mL) was added. The solution was neutralized to pH 2 using 20% HCl and the precipitate was filtered and washed with water. 4 was obtained as a grey powder (158 mg, 71% yield), mp: 260° C. (dec). $^1$H NMR (DMSO-d6, ppm): 11.62 (s, 1 H, NH), 9.77 (s, 1 H, NH), 7.98–7.97 (d, 1 H, J=1.4 Hz, Ar—H), 7.36–7.28 (m, 2 H, Ar—H), 7.02 (d, 1 H, J=1.5 Hz, Ar—H), 2.03 (s, 3 H, $CH_3CO$), Anal. ($C_{11}H_{10}N_2O_3.0.6H_2O$), C, H, N.

5-[[5-(Acetamino)-1H-indol-2-ylcarbonyl]amino]-1H-indol-2-carboxylic acid (6).

1-(3-Dimethylaminopropyl)-3-ethylcarbodiimide (EDCI, 268 mg) was added to a solution of 2 (94 mg, 0.46 mmol) and 4 (101 mg, 0.46 mmol) in DMF (3 mL) and the reaction mixture was stirred overnight at room temperature. Ethyl acetate (40 mL) was added and the mixture was washed with saturated sodium carbonate solution (10 mL) followed by water (20 mL×2). The solution was dried using sodium sulfate and solvent was removed in vacuo. A grey powder 5 was obtained (129 mg, 69% yield). $^1$H NMR (DMSO-d6, ppm): 11.82, (s, 1 H, NH), 11.57 (s, 1 H, NH), 10.09 (s, 1 H, NH), 9.77 (s, 1 H, NH), 8.13–7.15 (m, 8 H, Ar—H), 4.38–4.32 (q, 2 H, J=7.0, 13.7 Hz, $CH_2CH_3$). 2.04 (s, 3 H, $CH_3CO$), 1.37–1.33 (t, 3 H, J=7.0 Hz, $CH_2CH_3$). MS (ion spray, M/z) 404. Without further purification 3N NaOH (3 mL) was added to a solution of 5 (103 mg, 0.25 mmol) in DMF (3 mL) and methanol (15 mL) and the reaction mixture was stirred overnight at room temperature. The reaction mixture was evaporated and water (5 mL) was added. The solution was neutralized to pH 2 using 20% HCl and the precipitate was filtered and washed with water. 6 was obtained as a grey powder (45 mg, 48% yield), mp: >300° C. $^1$H NMR (DMSO-d6, ppm): 12.80 (br, 1 H, COOH), 11.69, (s, 1 H, NH), 11.57 (s, 1 H, NH), 10.06 (s, 1 H, NH), 9.77 (s, 1 H, NH), 8.12–7.09 (m, 8 H, Ar—H), 2.05 (s, 3 H, $CH_3CO$), Anal. ($C_{20}H_{16}N_4O_4.1.2H_2O$), C, H, N.

Methyl 5-acetaminobenzofuran-2-carboxylate (9). Methyl 5-nitrobenzofuran-2-carboxylate (13, 0.5 g, 2.26 mmol, made from 5-nitrobenzofuran-2-carboxylic acid, Trans World Chemicals, Inc.) was dissolved in ethyl acetate (40 mL) and 5% Pd/C (30 mg) was added. The reaction mixture was hydrogenated for 1 h at room temperature at a pressure of 60 lb/inch$^2$. The reaction mixture was filtered and the solvent was removed in vacuo. The residue was dissolved in acetone (10 mL) and was used without further purification. Acetic anhydride (0.86 mL, 9.1 mmol) and dimethylaminopyridine (20 mg) was added. The solution was stirred for 1 h at room temperature. Water (20 mL) was added and the mixture was extracted with ethyl acetate (40 mL×5). The solution was dried using sodium sulfate and solvent was removed in vacuo. A grey powder 9 was obtained (321 mg, 61% yield). An analytical sample was recrystallized in ethyl acetate. mp: 158°–159° C. $^1$H NMR (DMSO-d6, ppm): 10.03 (s, 1 H, NH), 8.19–8.18 (d, 1 H, J=1.6 Hz, Ar—H), 7.76–7.75 (d, 1 H, J=1.1 Hz, Ar—H), 7.65–7.63 (d, 1 H, J=9.0 Hz, Ar—H), 7.55–7.52 (dd, 2 H, J=2.3, 8.9 Hz, Ar—H), 3.89 (s, 1 H, $OCH_3$), 2.07 (s, 3 H, $CH_3CO$), Anal. ($C_{12}H_{11}NO_4$), C, H, N.

5-Acetaminobenzofuran-2-carboxylic acid (10). 3N NaOH (2 mL) was added to a solution of 9 (302 mg, 1.3 mmol) in methanol (20 mL) and the reaction mixture was stirred for 48 h at room temperature. Solvent was evaporated and water (20 mL) was added. The solution was neutralized to pH 2 using 20% HCl and the precipitate was filtered and washed with water. 10 was obtained as a grey powder (231 mg, 81% yield), mp: >300° C. $^1$H NMR (DMSO-d6, ppm): 13.30 (s, 1 H, COOH), 10.01 (s, 1 H, NH), 8.16–8.15 (d, 1 H, J=1.9 Hz, Ar—H), 7.65–7.60 (m, 2 H, Ar—H), 7.53–7.50 (dd, 2 H, J=1.6, 8.4 Hz, Ar—H), 2.07 (s, 3 H, $CH_3CO$), Anal. ($C_{11}H_9NO_4.0.3H_2O$), C, H, N.

5-[[5-(Acetamino)-1H-benzofuran-2-ylcarbonyl]amino]-1H-indol-2-carboxylic acid (12).

EDCI (523 mg) was added to a solution of 2 (186 mg, 0.91 mmol) and 16 (200 mg, 0.91 mmol) in DMF (3 mL) and THF (3 mL). The reaction mixture was stirred overnight at room temperature. Ethyl acetate (40 mL) was added and the mixture was washed with saturated sodium carbonate solution (10 mL) followed by water (20 mL×2), diluted HCl (10 mL), and water (20 mL). The solution was dried using sodium sulfate and solvent was removed in vacuo. Ether (20 mL) was added and a grey powder 11 was obtained (270 mg, 73% yield). $^1$H NMR (DMSO-d6, ppm): 11.84, (s, 1 H, NH), 10.38 (s, 1 H, NH), 10.03 (s, 1 H, NH), 8.15–7.15 (m, 8 H, Ar—H), 4.38–4.32 (q, 2 H, J=6.9, 13.7 Hz, CH$_2$CH$_3$). 2.08 (s, 3 H, CH$_3$CO), 1.37–1.33 (t, 3 H, J=6.8 Hz, CH$_2$CH$_3$). MS (ion spray, M+2H) 406. Without further purification 3N NaOH (3 mL) was added to a solution of 11 (140 mg, 0.35 mmol) in DMF (2 mL), acetone (10 mL), methanol (15 mL), water (5 mL) and the reaction mixture was stirred overnight at room temperature. Solvent was removed and water (20 mL) was added. The solution was neutralized to pH 2 using 20% HCl and the precipitate was filtered and washed with water. 12 was obtained as a grey powder (54 mg, 41% yield), mp: >300° C. $^1$H NMR (DMSO-d6, ppm): 12.80 (br, 1 H, COOH), 11.72, (s, 1 H, NH), 10.36 (s, 1 H, NH), 10.03 (s, 1 H, NH), 8.15–7.10 (m, 8 H, Ar—H), 2.08 (s, 3 H, CH$_3$CO), Anal. (C$_{20}$H$_{14}$N$_3$O$_5$1.1H$_2$O), C, H, N.

2-Hydroxymethyl-5-nitroindole (13).

Concentrated sulfuric acid (1.27 mL) was added dropwise to lithium aluminum hydride (1.89 g) in THF (100 mL) at 0° C. under N$_2$. The reaction mixture was stirred for 20 min at 0° C. A solution of 1 (2 g, 8.5 mmol) in THF (80 mL) was then added and the reaction mixture was stirred for 30 min at 0° C. Ice (10 g) was added carefully and the mixture was filtered. The filter cake was washed with ethyl acetate (200 mL). Water and solvent was removed in vacuo and the residue was dissolved in ethyl acetate. The solution was filtered through celite and the celite was washed with ethyl acetate (200 mL). The solvent was removed in vacuo and a grey solid 7 was obtained (1.48 g, 90% yield). An analytical sample was recrystallized in ethyl acetate. mp: 156°–157° C. $^1$H NMR (DMSO-d6, ppm): 11.77 (brs, 1 H, NH), 8.49–8.48 (d, 1 H, J=3.5 Hz, Ar—H), 7.97–7.93 (dd, 1 H, J=2.4, 9.0 Hz, Ar—H), 7.49–7.46 (d, 1 H, J=9.2 Hz, Ar—H), 6.57 (s, 1 H, Ar—H), 5.42–5.39 (t, 1 H. J=5.6 Hz, OH), 4.66–4.64 (d, 1 H, J=5.5 Hz, CH$_2$OH), Anal. (C$_9$H$_8$N$_2$O$_3$), C, H, N.

5-Amino-2-hydroxymethylindole (14).

To a solution of 13 (862 mg, 4.49 mmol) in methanol (50 mL) was added 5% Pd/C (50 mg) and the reaction mixture was hydrogenated for 1 h at a pressure of 50 lb/inch$^2$. The reaction mixture was filtered through celite and the celite was washed with methanol. The solvent was removed in vacuo and 707 mg (97% yield) of grey powder 14 was obtained. mp: 159°–160° C. $^1$H NMR (DMSO-d6, ppm): 10.44 (s, 1 H, NH), 7.01–6.99 (d, 1 H, J=8.5 Hz, Ar—H), 6.60 (d, 1 H, J=2.0 Hz, Ar—H), 6.43–6.40 (dd, 1 H, J=2.4, 8.5 Hz, Ar—H), 5.97 (brs, 1 H, Ar—H), 5.07 (brs, 1 H, OH), 4.50 (brs, 2 H, CH$_2$OH), 4.30 (brs, 2 H, NH$_2$), Anal. (C$_9$H$_{10}$N$_2$O), C, H, N.

5-Acetamino-2-hydroxymethylindole (15).

To a solution of 14 (200 mg, 1.25 mmol), dimethylaminopyridine (20 mg) and triethylamine (0.94 mL) in THF cooled to 0° C. was added a solution of acetyl chloride (0.30 mL, 4.16 mmol) in THF (5 mL) dropwise. The reaction mixture was allowed to warm up to room temperature and stirred for 3 h. THF was removed in vacuo and ethyl acetate (40 mL) was added. The solution was washed with water (20 mL×2). The solution was dried using sodium sulfate and solvent was removed in vacuo. The residue was dissolved in methanol (5 mL) and 3N NaOH solution(1 mL) was added. The reacted was allowed to proceed overnight. The reaction mixture was evaporated and water (10 mL) was added. The product was extracted with ethyl acetate (30 mL×3) and the solvent was removed in vacuo. The product was crystallized in acetate and washed with ether. 128 mg (50% yield) of grew powder 15 was obtained. mp: 161° C. $^1$H NMR (DMSO-d6, ppm): 10.84 (s, 1 H, NH), 9.62 (s, 1 H, NH), 7.75 (d, 1 H, J=2.1 Hz, Ar—H), 7.22–7.10 (m, 2 H, Ar—H), 6.20 (s, 1 H, Ar—H), 6.43–6.40 (dd, 1 H, J=2.4, 8.5 Hz, Ar—H), 5 5.18–5.15 (t, 1 H, J=5.5 Hz, OH), 4.57–4.56 (d, 2 H, J=5.4 Hz, CH$_2$OH), 2.01 (s, 3 H, CH$_3$), Anal. (C$_{11}$H$_{12}$N$_2$O$_2$), C, H, N.

5-Acetamino-2-indolecarboxaldehyde (16).

To a solution of 15 (100 mg, 0.5 mmol) in ethanol (10 mL) was added MnO$_2$ (250 mg) and the reaction mixture was stirred for 3 h at room temperature. The reaction mixture was filtered and the solid was washed with ethanol. The solvent was removed in vacuo and a grey solid 16 was obtained (97 mg, 100% yield). An analytical sample was recrystallized in ethyl acetate. mp: 200° C. (dec). $^1$H NMR (DMSO-d6, ppm): 11.80 (s, 1 H, NH), 9.84 (s, 1 H, NH), 9.81 (s, 1 H, CHO), 8.09 (s, 1 H, Ar—H), 7.38–7.32 (m, 3 H, Ar—H), 2.04 (s, 3 H, CH$_3$), Anal. (C$_{11}$H$_{10}$N$_2$O$_2$0.4H$_2$O), C, H, N.

5-Acetamino-2-indoleacrylic acid (18).

16 (340 mg, 0.7 mmol) was added to a solution of methyl(triphenylphosphoranylidene)acetate (2!57 mg, 0.77 mmol) in toluene (30 mL) and the reaction mixture was heated to reflux for 3 days. The solvent was removed after cooled to room temperature. Ethyl acetate (10 mL) was added to the residue and the resulted precipitate 17 was filtered. MS (ion spray) (M+H) 259. Without further purification 17 was dissolved in DMF (3 mL) and methanol (5 mL) was added. 3N NaOH solution (2 mL) was added and the reaction mixture was stirred overnight. The solvent was removed and water (10 mL) was added. The solution was neutralized using 20% HCl. The resulting precipitate was filtered and washed with water. 44 mg (26% yield) of yellow solid 18 was obtained. mp: 238°–239° C. $^1$H NMR (DMSO-d6, ppm): 12.25 (brs, 1 H, COOH), 11.42 (s, 1 H, NH), 9.74 (s, 1 H, NH), 7.88 (s, 1 H, Ar—H), 7.55–7.50 (d, 1 H, J=16.0 Hz, CH=CH), 7.28 (s, 2 H, Ar—H) 6.80 (d, 1 H, J=2.0 Hz, Ar—H), 6.44–6.40 (d, 1 H, J=15.8 Hz, CH=CH), 2.03 (s, 3 H, CH$_3$), Anal. (C$_{13}$H$_{12}$N$_2$O$_3$0.3H$_2$O), C, H, N.

5-[(1H-Benzofuran-2-ylcarbonyl)amino]-2-hydroxymethylindole (20).

EDCI (597 mg) was added to a solution of 2 (169 mg, 1.04 mmol) and benzofuran-2-carboxylic acid 19 (168 mg, 1.04 mmol) in DMF (2 mL). The reaction mixture was stirred overnight at room temperature. Ethyl acetate (40 mL) was added and the mixture was washed with saturated sodium carbonate solution (8 mL) followed by water (20 mL×2). The solution was dried using sodium sulfate and solvent was removed in vacuo. The product was purified by flush column chromatography eluting with ethyl acetate and crystallized in ether. A grey powder 20 was obtained (223 mg, 70% yield). mp: 164°–165° C. $^1$H NMR (DMSO-d6, ppm): $^1$H NMR (DMSO-d6, ppm): 10.96, (s, 1 H, NH), 10.27 (s, 1 H, NH), 7.93–7.29 (m, 8 H, Ar—H), 6.27 (s, 1 H, Ar—H), 5.22–5.19 (t, 1 H, J=5.6 Hz, OH), 4.61–4.60 (d, 2 H, CH$_2$). Anal. (C$_{18}$H$_{14}$N$_2$O$_3$), C, H, N.

5-[(1H-Benzofuran-2-ylcarbonyl)amino]-2-indolecarboxaldehyde (21).

To a solution of 20(100 mg, 0.33 mmol) in ethanol (15 mL) was added MnO$_2$ (0.5 g) and the reaction mixture was stirred for 4 h at room temperature. The reaction mixture was filtered through celite and the solid was washed with ethanol. Solvent was removed in vacuo and a grey solid 21 was obtained (54 mg, 54% yield). An analytical sample was recrystallized in ethyl acetate. mp: 253° C. (dec). $^1$H NMR (DMSO-d6, ppm): 10.60 (brs, 1 H, NH), 9.85, (s, 1 H, NH), 8.26 (s, 1 H, CHO), 7.84–7.35 (m, 9 H, Ar—H). Anal. ($C_{18}H_{12}N_2O_3.0.3H_2O$), C, H, N.

Methyl 5-[(1H-benzofuran-2-ylcarbonyl)amino]-2-indoleacrylate (22).

21 (100 mg, 0.33 mmol) was added to a solution of methyl(triphenylphosphoranylidene)acetate (120 mg, 0.36 mmol) in toluene (30 mL) and the reaction mixture was heated to reflux for 4 days. The solvent was removed after cooled to room temperature. The product was crystallized in a solution of acetone and ether. The mother liquid was then purified by flush column chromatography eluting with ethyl acetate and hexane (1/2, v/v). A total of 78 mg (66% yield) of yellow solid 22 was obtained. mp: 259°–260° C. $^1$H NMR (DMSO-d6, ppm): 11.57 (s, 1 H, NH), 10.38 (s, 1 H, NH), 8.07–7.35 (m, 9 H, Ar—H, CH=CH), 6.93 (s, 1 H, Ar—H), 6.57–6.53 (d, 1 H, J=15.8 Hz, CH=CH), 3.74 (s, 3 H, CH$_3$). Anal. ($C_{21}H_{16}N_2O_4$), C, H, N.

5-[(1H-Benzofuran-2-ylcarbonyl)amino]-2-indoleacrylic acid (23).

22 (60 mg, 0.167 mmol) was dissolved in DMF (1.5 mL) and ethanol (3 mL) was added. 3N NaOH solution (1.5 mL) was added and the reaction mixture was stirred overnight. The solvent was removed and water (10 mL) was added. The solution was neutralized using 20% HCl. The resulting precipitate was filtered and washed with water. 53 mg (92% yield) of yellow solid 23 was obtained. mp: 268° C. (dec). $^1$H NMR (DMSO-d6, ppm): 12.27 (brs, 1 H, COOH), 11.53 (s, 1 H, NH), 10.38 (s, 1 H, NH), 8.07–7.35 (m, 9 H, Ar—H, CH=CH), 6.88 (s, 1 H, Ar—H), 6.48–6.44 (d, 1 H, J=16.2 Hz, CH=CH). Anal. ($C_{20}H_{14}N_2O_4.0.4H_2O$), C, H, N.

5-[(4-Hydroxy)butyramino]indole-2-carboxylic acid (25).

A solution of 1 (2.5 g, 10.7 mmol) in ethyl acetate (200 mL) was treated with 10% palladium on activated carbon (0.6 g), and was then hydrogenated for 1 h at room temperature. The reaction mixture was filtered through Celite and the filter cake was washed with ethyl acetate. The combined organic solution was concentrated in vacuo. Without further purification the resulting oil was dissolved in butyrolactone (20 mL) and the solution was stirred for 18 h at 130° C. The product was purified by flash chromatography eluting with 30% hexane in ethyl acetate to give 24 (1.37 g, 44% yield) as a yellow solid. $^1$H NMR (DMSO-d$_6$, ppm) 11.72 (s, 1 H, NH), 9.73 (s, 1 H, CONH), 8.00–7.07 (m, 4 H, Ar—H), 4.47–4.44 (t, 1 H, J=4.8 Hz, OH), 4.36–4.30 (q, 2 H, J=7.0, 14.2 Hz, CH$_2$CH$_3$), 3.47–3.42 (q, 2 H, J=6.1, 11.4 Hz, HOCH$_2$), 2.36–2.32 (t, 2 H, J=7.4 Hz, COCH$_2$), 1.77–1.73 (m, 2 H, CH$_2$CH$_2$CH$_2$), 1.36–1.32 (t, 3 H, J=7.2, CH$_2$CH$_3$). A solution of compound 24 (1.0 g, 3.4 mmol) in methanol (150 mL) was treated with 3N sodium hydroxide solution (20 mL), and was stirred for 18 h at room temperature. The solution was then concentrated in vacuo. Water was added (100 mL). The solution was neutralized with 20% hydrochloric acid and the precipitate was filtered to afford compound 25 (723 mg, 65% yield) as a brown solid. m.p.194°–195° C. $^1$H NMR (DMSO-d$_6$, ppm) 12.80 (brs, 1 H, COOH), 11.60 (s, 1 H, NH), 9.72 (s, 1 H, CONH), 7.99–7.02 (m, 4 H, Ar—H), 3.47–3.43 (t, 2 H, J=6.8, HOCH$_2$), 2.37–2.32 (t, 2 H, J=7.4, COCH$_2$), 1.77–1.73 (m, 2 H, CH$_2$CH$_2$CH$_2$) Anal. ($C_{13}H_{14}N_2O_4$), C, H, N.

Benzyl 5-[(4-hydroxy)butyramino]indole-2-carboxylate (26).

A solution of compound 7 (810 mg, 3.1 mmol) in DMF (15 mL) was treated with sodium bicarbonate (1.6 g, 19.0 mmol), and benzyl bromide (540 mL, 4.5 mmol), and the reaction mixture was stirred for 18 h at room temperature. The reaction was quenched with water (80 mL) and the product was extracted with ethyl acetate (50 mL×5). The solution was dried using sodium sulfate and concentrated in vacuo. The product was purified by flash chromatography eluting with 50% hexane in ethyl acetate to give compound 26 (778 mg, 71% yield) as a solid. m.p. 191°–192° C. $^1$H NMR (DMSO-d$_6$, ppm) 11.78 (s, 1 H, NH), 9.73 (s, 1 H, CONH), 8.00–7.14 (m, 9 H, Ar—H), 5.37 (s, 2 H, CH$_2$C$_6$H$_5$), 4.46–4.44 (t, H, J=5.2 Hz, OH), 3.47–3.42 (q, 2 H, J=6.6, 11.7 Hz, HOCH$_2$), 2.36–2.32 (t, 2 H, J=7.4, COCH$_2$), 1.78–1.71 (m, 2 H, CH$_2$CH$_2$CH$_2$). Anal. ($C_{20}H_{20}N_2O_4.0.3H_2O$), C, H, N.

5-[4-(Methyl 2,3,4-tri-O-acetyl-1-deoxy-b-D-glucuronate) butyramino]indole-2-carboxylic acid (29).

Molecular sieves (1 g) was added to a solution of compound 26 (778 mg, 2.21 mmol) in THF (20 mL) and dichloromethane (20 mL), and the temperature was cooled to −60° C. under nitrogen. Methyl 2,3,4-tri-O-acetyl-1-bromo-1-deoxy-a-D-glucuronate (27, 1.32 g, 3.3 mmol), silver trifluoromethanesulfonate (852 mg, 3.3 mmol) and silver carbonate (922 mg, 3.3 mmol) was added sequentially and the reaction mixture was stirred for 10 min. The temperature was allowed to warm up to room temperature and the stirring was continued for 2 h at dark. The mixture was filtered through Celite and the filter cake washed with ethyl acetate. The solution was dried with sodium sulfate, concentrated in vacuo. the product was purified by flash chromatography eluting with 50% hexane in ethyl acetate to give compound 28 as a white foam. $^1$H NMR (acetone-d$_6$, ppm): 8.88 (s, 1 H, CONH), 7.95 (s, 1 H, Ar—H), 7.47–7.21 (m, 9 H, Ar—H), 5.86–5.85 (d, 1 H, J=4.5 Hz, sugar C1—H), 5.38 (s, 2 H, CH$_2$C$_6$H$_5$), 5.22–5.21 (t, 1 H, J=2.4 Hz, sugar C2—H), 5.16–5.14 (m, 1 H, sugar C4—H), 4.34–4.30 (m, 2 H, sugar C3—H, C5—H), 3.76 (s, 3 H, COOCH$_3$), 3.63–3.59 (m, OCH$_2$), 2.47–2.44 (t, 2 H, J=6.7 Hz, CH$_2$CO), 2.17 (s, 3 H, CH$_3$CO), 2.08 (s, 3 H, CH$_3$CO) 2.03–2.00 (m, 2 H, CH$_2$CH$_2$CH$_2$), 1.75 (s, 3 H, CH$_3$CO). Without further purification the foam was dissolved in ethyl acetate (15 mL), treated with 10% palladium on activated charcoal (600 mg), and then hydrogenated for 1 h at room temperature. The mixture was filtered through Celite and the filter cake was washed with ethyl acetate. The combined organics were concentrated in vacuo to give compound 29 (846 mg, 66%) as a white foam which crystallized from petroleum ether. m.p. 94°–96° C. $^1$H NMR (DMSO-d$_6$, ppm) 11.43 (s, 1 H, NH), 9.69 (s, 1 H, CONH), 7.94–6.91 (m, 4 H, Ar—H), 5.88–5.87 (d, 1 H, J=4.2 Hz, sugar C1—H), 5.09–5.07 (t, 1 H, J=3.2 Hz, sugar C2—H), 5.05–5.02 (m, 1 H, sugar C4—H), 4.42–4.40 (d, 1 H, J=6.2 Hz, sugar C5—H), 4.36–4.35 (t, 1 H, J=3.3 Hz, sugar C3—H), 3.69 (S, 3 H, COOCH$_3$), 3.51–3.48 (t, 2 H, J=6.4 Hz, OCH$_2$), 2.37–2.33 (t, 2 H, J==7.6 Hz, CH$_2$CO), 2.05 (s, 3 H, CH$_3$CO), 2.02 (s, 3 H, CH$_3$CO), 1.82–1.79 (m, 2 H, CH$_2$CH$_2$CH$_2$), 1.65 (S, 3 H, CH$_3$CO).

Ethyl 5-(tert-butyloxycarbonylamino)indole-2-carboxylate (30).

A solution of compound 1 (2.5 g, 10.7 mmol) in ethyl acetate (200 mL) was treated with 10% palladium on activated charcoal (200 mg), and then hydrogenated for 1 h at room temperature. The mixture was filtered through Celite and the filter cake was washed with ethyl acetate. The combined organics were concentrated in vacuo. The residue was dissolved in ethyl acetate (150 mL), and treated with di-tert-butyl dicarbonate (5.8 g, 26.6 mmol) and the reaction mixture was stirred for 18 h at room temperature. The reaction was quenched with water (40 mL) and the ethyl acetate solution was, separated. The solution was dried with sodium sulfate, concentrated in vacuo to give compound 30 (2.61 g, 80%) as a yellow solid, m.p. 190°–192° C. $^1$H NMR (DMSO-d$_6$, ppm): 11.69 (s, 1 H, NH), 9.13 (s, 1 H, CONH), 7.79–7.04 (m, 4 H, Ar—H), 4.35–4.30 (q, 2 H, J=6.8, 13.9 Hz, CH$_2$CH$_3$), 1.48 (s, 9 H, C(CH$_3$)$_3$), 1.35–1.31 (t, 3 H, J=6.7, CH$_2$CH$_3$). Anal. (C$_{16}$H$_{20}$N$_2$O$_4$), C, H, N.

5-(tert-Butyloxycarbonylamino)indole-2-carboxylic acid (31).

A solution of compound 30 (2.61 g, 8.6 mmol) in methanol (200 mL) was treated with 3N sodium hydroxide solution (50 mL), and the reaction mixture was stirred for 18 h at room temperature. Solvent was removed. Water (100 mL) was added. The solution was neutralized with 20% hydrochloric acid and the precipitate was filtered to give compound 31 (2.03 g, 86%) as a yellow solid. m.p.192°–193° C. $^1$H NMR (DMSO-d$_6$, ppm) 12.83 (brs, 1 H, COOH), 11.69 (s, 1 H, NH), 9.13 (s, 1 H, CONH), 7.79–7.04 (m, 4 H, Ar—H), 1.48 (s, 9 H, C(CH$_3$)$_3$). Anal. (C$_{14}$H$_{16}$N$_2$O$_4$.H$_2$O), C, H, N.

Benzyl 5-(tert-butyloxycarbonylamino)indole-2-carboxylate (32).

A solution of compound 31 (2.03 g, 7.4 mmol) in DMF (50 mL) was treated with sodium bicarbonate (1.8 g, 21.4 mmol), and benzyl bromide (4 mL, 33.6 mmol). The reaction mixture was stirred for 18 h at room temperature. Water (50 mL) was added and the product was extracted with ethyl acetate (80 mL×3). The solution was dried with sodium sulfate, concentrated in vacuo to give compound 32 (2.27 g, 84% yield) as a white solid. m.p.180°–182° C. $^1$H NMR (DMSO-d$_6$, ppm): 11.93 (s, 1 H, NH), 7.51–7.02 (m, 9 H, Ar—H), 5.38 (s, 2 H, CH$_2$C$_6$H$_5$), 1,48 (s, 9 H, C(CH$_3$)$_3$). Anal. (C$_{21}$H$_{22}$N$_2$O$_4$.0.25H$_2$O), C, H, N.

Benzyl 5- [[5-[4-(hydroxy)butyramino]-1H-indol-2-ylcarbonyl]amino]-1H-indol-2-carboxylate (34).

Compound 33 from 32 (280 mg, 0.77 mmol) in DMF (1 mL) was treated with 25 (200 mg, 0.76 mmol) and 1-(3-dimethylaminopropyl)-3-ethylcarbodiimide (EDCI, 440 mg, 2.30 mmol), and the reaction mixture was stirred for 18 h at room temperature, then diluted with water (20 mL), extracted with ethyl acetate (50 mL×3). The organic layer was dried with sodium sulfate and concentrated in vacuo. The product was purified by flash chromatography eluting with ethyl acetate to give 34 (232 mg, 60% yield) as a pale yellow solid. m.p. 242°–243° C. $^1$H NMR (DMSO-d$_6$, ppm): 11.87 (s, 1 H, NH), 11.55 (s, 1 H, NH), 10.08 (s, 1 H, CONH), 9.71 (s, 1 H, CONH), 8.13–7.22 (m, 13 H, Ar—H), 5.39 (s, 2 H, CH$_2$C$_6$H$_5$), 4.47–4.45 (t, 1 H, J=5.1 Hz, OH), 3.48–3.44 (q, 2 H, J=6.4, 11.9 Hz, HOCH$_2$), 2.38–2.33 (t, 2 H, J=7.5 Hz, COCH$_2$), 1.78–1.74 (m, 2 H, CH$_2$CH$_2$CH$_2$).

5-[[5-[4-(Hydroxy)butyramino]-1H-indol-2-ylcarbonyl]amino]-1H-indol-2-carboxylic acid (35).

A solution of 3–4 (230 mg, 0.45 mmol) in DMF (1 mL) and methanol (20 mL) was treated with 10% palladium in activated carbon (20 mg), and hydrogenated for 1 h at room temperature. The mixture was filtered through Celite and the filter cake washed with methanol. The combined organics were concentrated in vacuo to give 35 (160 mg, 84%) as a white solid. m.p. 249°–251° C. $^1$H NMR (DMSO-d$_6$, ppm): 12.75 (s, 1 H, COOH), 11.68 (s,1 H, NH), 11.54 (s, 1 H, NH), 10.05 (s, 1 H, CONH), 9.70 (s, 1 H, CONH), 8.12–7.09 (m, 8 H, Ar—H), 4.47–4.44 (t, 1 H, J=5.4 Hz, OH), 3.49–3.44 (q, 2 H, J=6.4, 11.0 Hz, HOCH$_2$), 2.38–2.34 (t, 2 H, J=7.4 Hz, COCH$_2$), 1.80–1.74 (m, 2 H, CH$_2$CH$_2$CH$_2$)

Benzyl 5-[[5-[5-[4-(methyl 2,3,4-tri-O-acetyl-1-deoxy-b-D-glucuronate)butyramino]-1H-indo 1-2-ylcarbonyl]amino]-1H-indol-2-carboxylate (37).

A solution of compound 32 (280 mg, 0.77 mmol) in ethyl acetate (20 mL) saturated with hydrogen chloride was refluxed for 30 min. The suspension was concentrated in vacuo to give a solid which was then treated with triethylamine (6 mL) in ethyl acetate (20 mL). The reaction mixture was stirred at room temperature for 10 min and filtered. The solution was concentrated in vacuo to afford 33. Without further purification the latter was dissolved in DMF (1 mL), and treated with compound 36 (200 mg, 0.35 mmol), 1,3-dicyclohexylcarbodiimide (DCC, 214 mg, 1.04 mmol) and 1-hydroxybenzotriazole hydrate (HOBT, 140 mg, 1.04 mmol). The reaction mixture was stirred at room temperature for 2 h, then diluted with water (10 mL), extracted with ethyl acetate (50 mL×3). The solution was dried with sodium sulfate, concentrated in vacuo. The product was purified by flash chromatography eluting with a solution of hexane and ethyl acetate (3/7, v/v) to afford 37 (230 mg, 80% yield) as a yellow solid, m.p. 143°–145° C. $^1$H NMR (DMSO-d$_6$, ppm): 11.87 (s, 1 H, NH), 11.56 (s, 1 H, NH), 10.08 (s, 1 H, CONH), 9.73 (s, 1 H, CONH), 8.14–7.22 (m, 13 H, Ar—H), 5.89–5.88 (d, 1 H, J=4.4 Hz, sugar C1—H), 5.39 (s, 2 H, CH$_2$C$_6$H$_5$), 5.09–5.08 (t, 1 H, J=2.9 Hz, sugar C2—H), 5.05–5.02 (m, 1 H, sugar C4—H), 4.43–4.41 (d, 1 H, J=6.7 Hz, sugar C5—H), 4.37–4.35 (t, 1 H, J=3.4 Hz, sugar C3—H), 3.69 (s, 3 H, COOCH$_3$), 3.52–3.49 (t, 2 H, J=6.4 Hz, OCH$_2$), 2.39–2.34 (t, 2 H, J=7.7 Hz, COCH$_2$), 2.05 (,3, 3 H, CH$_3$CO), 2.03 (s, 3 H, CH$_3$CO), 1.84–1.80 (m, 2 H, CH$_2$CH$_2$CH$_2$), 1.66 (s, 3 H, CH$_3$CO).

5-[[5-[4-(Methyl 2,3,4-tri-O-acetyl-1-deoxy-b-D-glucuronate)butyramino]-1H-indo 1-2-ylcarbonyl]amino]-1H-indol-2-carboxylic acid (38).

A solution of 37 (230 mg, 0.28 mmol) in ethyl acetate (35 mL) was treated with 10% palladium on activated charcoal (20 mg), and then hydrogenated for 1 h at room temperature. The mixture was filtered through Celite and the filter cake was washed with ethyl acetate. The combined organics were concentrated in vacuo to give compound 38 (176 mg, 86% yield) as a yellow oil which crystallized from ether on standing. m.p. 76°–79° C. $^1$H NMR (DMSO-d$_6$, ppm): 12.81 (brs, 1 H, COOH), 11.67 (s, 1 H, NH), 11.54 (s, 1 H, NH), 10.05 (s, 1 H, CONH), 9.72 (s, 1 H, CONH), 8.12–7.08 (m, 8 H, Ar—H), 5.89–5.88 (d, 1 H, J=4.7 Hz, sugar C1—H), 5.09–5.08 (t, 1 H, J=3.0 Hz, sugar C2—H), 5.05–5.03 (m, 1 H, sugar C4—H), 4.42–4.41 (d, 1 H, J=6.6 Hz, sugar C5—H), 4.37–4.35 (t, 1 H, J=3.2 Hz, sugar C3—H), 3.69 (s, 3 H, COOCH$_3$), 3.52–3.49 (t, 2 H, J=5.8 Hz, OCH$_2$), 2.39–2.34 (t, 2 H, J=7.8 Hz, COCH$_2$), 2.05 (s, 3 H, CH$_3$CO), 2.03 (s, 3 H, CH$_3$CO), 1.84–1.80 (m, 2 H, CH$_2$CH$_2$CH$_2$), 1,66 (s, 3 H, CH$_3$CO).

Benzyl 5-[[5-[[5-[4-(methyl 2,3,4-tri-O-acetyl-1-deoxy-b-D-glucuronate)butyramino]-1H-indo 1-2-ylcarbonyl] amino]-1H-indol-2-ylcarbonyl]amino]-1H-indol-2-carboxylate (39).

39 was synthesized using a similar procedure as that described for 37 (98% yield) as a yellow solid. $^1$H NMR (DMSO-d$_6$, ppm): 11.88 (s, 1 H, 1H), 11.66 (s, 1 H, NH), 11.58 (s, 1 H, NH), 10.12 (s, 1 H, CONH), 10.07 (s, 1 H, CONH), 9.73 (s, 1 H, CONH), 8.16–7.23 (m, 17 H, Ar—H), 5.89–5.88 (d, 1 H, J=4.5 Hz, sugar C1—H), 5.40 (s, 2 H, CH$_2$C$_6$H$_5$), 5.09–5.08 (t, 1 H, J=2.5 Hz, sugar C2—H), 5.05–5.04 (m, 1 H, sugar C4—H), 4.43–4.41 (d, 1 H, J=6.6 Hz, sugar C5—H), 4.37–4.35 (t, 1 H, J=3.4 Hz, sugar C3—H), 3.69 (s, 3 H, COOCH$_3$), 3.52–3.49 (t, 2 H, J=6.4 Hz, OCH$_2$), 2.39–2.34 (t, 2 H, J=7.7 Hz, COCH$_2$), 2.05 (s, 3 H, CH$_3$CO), 2.03 (s, 3 H, CH$_3$CO), 1.84–1.80 (m, 2 H, CH$_2$CH$_2$CH$_2$), 1,66 (s, 3 H, CH$_3$CO).

5-[[5-[[5-[4-(Methyl 2,3,4-tri-O-acetyl-1-deoxy-b-D-glucuronate)butyramino]-1H-indo 1-2-ylcarbonyl]amino]-1H-indol-2-ylcarbonyl]amino]-1H-indol-2-carboxylic acid (40).

40 was synthesized using a similar procedure as that described for 38 (86% yield) as a yellow solid. 1H NMR (DMSO-d$_6$, ppm): 11.66 (s, 1 H, NH), 11.60 (s, 1 H, NH), 11.47 (s, 1 H, NH), 10.09 (s, 1 H, CONH), 10.08 (s, 1 H, CONH), 9.73 (s, 1 H, CONH), 8.14–6.97 (m, 12 H, Ar—H), 5.89–5.88 (d, 1 H, J=4.4 Hz, sugar C1—H), 5.10–5.08 (t, 1 H, J=3.1 Hz, sugar C2—H), 5.06–5.03 (m, 1 H, sugar C4—H), 4.43–4.41 (d, 1 H, J=6.6 Hz, sugar C5—H), 4.38–4.36 (t, 1 H, J=3.3 Hz, sugar C3—H), 3.69 (s, 3 H, COOCH$_3$), 3.54–3.51 (t, 2 H, J=6.3 Hz, OCH$_2$), 2.39–2.35 (t, 2 H, J=7.8 Hz, COCH$_2$), 2.05 (s, 3 H, CH$_3$CO), 2.03 (s, 3 H, CH$_3$CO), 1.86–1.80 (m, 2 H, CH$_2$CH$_2$CH$_2$), 1,66 (s, 3 H, CH$_3$CO).

Example 2
3-[[5-(acetamino)-1H-indol-2'-yl]carbonyl]-1-(chloromethyl)-5-hydroxy-1,2-dihydro-3H-benz[e]indole (YW-198).

EDCI (58 mg) was added to a solution of 41 (23 mg, 0.1 mmol), synthesized according a reported procedure (Aristoff, et al., *J. Med. Chem.*, 1993, 36, 1956) and compound 4 (23 mg, 0.11 mmol) in DMF (1 mL). The reaction mixture was stirred overnight at room temperature. The product was purified by thin layer chromatography eluting with ethyl acetate. A grey powder YW-198 was obtained (9.5 mg, 22% yield). $^1$H NMR (DMSO-d6, ppm): 11.57 (s, 1 H, NH), 10.52 (s, 1 H, OH), 9.89 (s, 1 H, NH), 8.25–7.23 (m, 9 H, Ar—H), 4.90–4.85 (dd, 1 H, J=9.6, 11.0 Hz, NHH), 4.75–4.71 (dd, 1 H, J=1.8, 10.6 Hz, NHH), 4.35–4.28 (m, 1 H, ClCH$_2$CHCH$_2$), 4.14–4.10 (dd, 1 H, J=3.4, 11.1 Hz, CHHCl), 3.97–3.92 (dd, 1 H, J=8.0, 11.1 Hz, CHHCl), 2.12 (s, 3 H, CH$_3$).

Example 3
3-[[5-[[5-(Acetamino)-1H-indol-2-ylcarbonyl]amino]-1H-indol-2-yl]carbonyl]-1-(chloromethyl)-5-hydroxy-1,2-dihydro-3H-benz[e]indole (YW-200).

YW-200 was synthesized using a similar procedure as that described for YW-198 except that 6 was used to afford a grey powder (80% yield). $^1$H NMR (DMSO-d6, ppm): 11.63 (s, 1 H, NH), 11.61 (s, 1 H, NH), 10.51 (s, 1 H, OH), 10.12 (s, 1 H, NH), 9.84 (s, 1 H, NH), 8.38–7.29 (m, 13 H, Ar—H), 4.92–4.86 (dd, 1 H, J=9.6, 11.0 Hz, NHH), 4.77–4.74 (dd, 1 H, J=1.8, 10.6 Hz, NHH), 4.36–4.28 (m, 1 H, ClCH$_2$CHCH$_2$), 4.15–4.11 (dd, 1 H, J=3.0, 10.8 Hz, CHHCl), 3.98–3.93 (dd, 1 H, J=7.9, 11.0 Hz, CHHCl), 2.04 (s, 3 H, CH$_3$).

Example 4
3-[[5-[[5-(Acetamino)-1H-benzofuran-2-ylcarbonyl]amino]-1H-indol-2-yl]carbonyl]-1-(chloromethyl)-5-hydroxy-1,2-dihydro-3H-benz[e]indole (YW-201).

YW-201 was synthesized using a similar procedure as that described for YW-198 except that 12 was used to afford a grey powder (53% yield). $^1$H NMR (DMSO-d6, ppm): 11.66 (s, 1H, NH), 10.51 (s, 1 H, OH), 10.46 (s, 1 H, NH), 10.10 (s, 1 H, 5 NH), 8.42–7.30 (m, 13 H, Ar—H), 4.92–4.88 (t, 1 H, J=10.2 Hz, NHH), 4.77–4.74 (dd, 1 H, J=1.8, 10.9 Hz, NHH), 4.36–4.28 (m, 1 H, ClCH$_2$CHCH$_2$), 4.15–4.11 (dd, 1 H, J=2.7, 10.7 Hz, CHHCl), 3.98–3.93 (dd, 1 H, J=7.7, 11.0 Hz, CHHCl), 2.10 (s, 3 H, CH$_3$).

Example 5
N$^2$-[[5-[[[5-(Acetamino)-1H-benzofuran-2-yl]carbonyl]amino]-1H-indol-2-yl]carbonyl]1,2,9,9a-tetrahydrocyclopropa[c]-benz[e]indol-4-one (YW-213).

YW-201 was dissolved in a solution of acetonitrile (3 mL), triethylamine (1 mL) and water (1 mL) and stirred at room temperature for 1 h. Solvent was removed in vacuo and the product was purified by thin layer chromagraphy eluting using ethyl acetate and hexane (3/1, v/v) to rproduce 8.7 mg of a grey solid. $^1$H NMR (DMF-d7, ppm): 11.88 (s, 1 H, NH), 10.51 (s, 1 H, NH), 10.15 (s, 1 H, NH), 8,21–6.97 (m, 13 H, Ar—H), 4.66–4.61 (dd, 1 H, J=5.0, 11.3 Hz, C1—H), 4.52–4.49 (d, 1 H, J=10.2 Hz, C1—H), 3.07–3.05 (m, 1 H, C9a—H), 2.10 (s,3 H, CH$_3$), 1.78–1.75 (dd, 1 H, J=3.6, 7.3 Hz, C9—H), 1.72–1.70 (t,1 H, J=4.9 Hz, C9—H).

Example 6
3-[[5-(acetamino)-1H-indol-2-yl]acrylyl]-1-(chloromethyl)-5-hydroxy-1,2-dihydro-3H-benz[e]indole(YW-202).

YW-202 was synthesized using a similar procedure as that described for YW-198 except that 16 was used to afford a grey powder (13% yield). $^1$H NMR (DMSO-d6, ppm): 11.69 (s, 1 H, NH), 10.52 (s, 1 H, OH), 9.82 (s, 1 H, NH), 8.28–6.90 (m, 11 H, Ar—H), 4.55–4.54 (d, 1 H, J=4.7 Hz, NHH), 4.27–4.23 (m, 2 H, NHH, ClCH$_2$CHCH$_2$), 4.12–4.08 (dd, 1 H, J=3.1, 1.0 Hz, CHHCl), 3.91–3.85 (dd, 1 H, J 8.8, 11.1 Hz, CHHCl), 2.12 (s, 3 H, CH$_3$).

Example 7
3-[[5-[(1H-Benzofuran-2-ylacrylyl)amino]-1H-indol-2-yl]carbony 1]-1-(chloromethyl)-5-hydroxy-1,2-dihydro-3H-benz[e]indole(YW-215).

YW-215 was synthesized using a similar procedure as that described for YW-198 except that 23 was used to afford a grey powder (55% yield). $^1$H NMR (DMSO-d6, ppm): 11.82 (s, 1 H, NH), 11.68 (s, 1 H, NH), 10.51 (s, 1 H, OH), 10.45 (s, 1 H, NH), 8.43–6.98 (m, 16 H, Ar—H), 4.90–4.87 (dd, 1 H, J=9.2, 11.1 Hz, NHH), 4.77–4.74 (dd, 1 H, J=2.2, 10.9 Hz, NHH), 4.36–4.28 (m, 1 H, ClCH$_2$CHCH$_2$), 4.15–4.11 (dd, 1 H, J=3.3, 11.3 Hz, CHHCl), 3.99–3.93 (dd, 1 H, J=8.1, 10.8 Hz, CHHCl).

Example 8
3-[[5-[(4-Hydroxy)butyramino]-1H-indol-2'-yl]carbonyl]-1-(chloromethyl)-5-hydroxy-1,2-dihydro-3H-benz[e]indole (YW-231).

YW-231 was synthesized using a similar procedure as that described for YW-198 except that 25 was used to afford a yellow solid (36% yield) as a yellow solid. $^1$H NMR (acetone-d$_6$, ppm): 10.73 (s, 1 H, NH), 9.27 (s, 1 H, Ar—OH), 9.08 (s, 1 H, CONH), 8.27–7.20 (m, 9 H, Ar—H), 4.84–4.80 (m, 2 H, NCH$_2$), 4.33–4.26 (m, 1 H, ClCH$_2$CH), 4.09–4.05 (dd, 1 H, J=3.6, 11.2 Hz, ClCHH), 3.85–3.79 (dd, 1 H, J=8.5, 11.2 Hz, ClCHH), 3.73–3.69 (t, 1 H, J=5.6, CH$_2$O) 3.66–3.61 (q, 2 H, J=5.9, 11.5 Hz, CH2OH), 2.51–2.47 (t, 2 H, J=7.1, Hz, COCH$_2$), 1.92–1.89 (m, 2 H, CH$_2$CH$_2$CH$_2$).

Example 9
3-[[5-[4-(Methyl 2,3,4-tri-O-acetyl-1-deoxy-b-D-glucuronate) butyramino]-1H-indol-2'-yl]carbonyl]-1-(chloromethyl)-5-hydroxy-1,2-dihydro-3H-benz[e]indole (YW-247).

YW-247 was synthesized using a similar procedure as that described for YW-198 except that 29 was used to afford a yellow solid (12% yield). $^1$H NMR (DMF-d$_6$, ppm): 11.56 (s, 1 H, NH), 10.5 (brs, 1 H, OH), 9.84 (s, 1 H, CONH), 8.25–7.23 (m, 9 H, Ar—H), 5.99–5.98 (d, 1 H, J=4.1 Hz, sugar C1—H), 5.22–5.20 (t, 1 H, J=2.9 Hz, sugar C2—H), 5.15–5.13 (m, 1 H, sugar C4—H), 4.90–4.84 (t, 1 H, J=8.6, NCHH), 4.75–4.71 (dd, 1 H, J=1.1, 12.2 Hz, NCHH), 4.51–4.48 (m, 2 H, sugar C3—H, C5—H), 4.33–4.28 (m, 1 H, ClCH$_2$CH), 4.14–4.10 (dd, 1 H, J=2.6, 10.6 Hz, ClCHH), 3.96–3.91 (dd, 1 H, J=7.8, 10.9 Hz, ClCHH), 3.77 (s, 3 H, COOCH$_3$), 3.63–3.59 (t, 2 H, J=6.9 Hz, OCH$_2$), 2.50–2.46 (t, 2 H, J=7.1 Hz, COCH$_2$), 2.10 (s, 3 H, CH$_3$CO), 2.08 (s, 3 H, CH$_3$CO), 1.96–1.90 (m, 2 H, CH$_2$CH$_2$CH$_2$), 1,72 (s, 3 H, CH$_3$CO).

Example 10
3-[[5-[[5-[4-(Hydroxy)butyramino]-1H-indol-2-ylcarbonyl]amino]-1H-indol-2-yl]carbonyl]-1-(chloromethyl)-5-hydroxy-1,2-dihydro-3H-benz[e]indole (YW-254).

YW-254 was synthesized using a similar procedure as that described for YW-198 except that 35 was used to afford a yellow solid (19% yield). $^1$H NMR (DMF-d$_6$, ppm): 11.74 (s, 1 H, NH), 11.62 (s, 1 H, NH), 10.47 (s, 1 H, Ar—OH), 10.44 (s, 1 H, CONH), 9.89 (s, 1 H, CONH), 8.43–7.06 (m, 13 H, Ar—H), 4.95–4.86 (m, 1 H, NCHH), 4.76–4.72 (m, 1 H, NCHH), 4.60–4.54 (brs, 1 H, CH$_2$OH), 4.34–4.28 (m, 1 H, ClCH$_2$CBH), 4.15–4.11 (dd, 1 H, J=3.2, 10.7 Hz, ClCHH), 3.98–3.93 (dd, 1 H, J=8.2, 11.1 Hz, ClCHH), 3.66–3.64 (m, 2 H, CH$_2$OH), 2.52–2.48 (t, 2 H, J=7.4, Hz, COCH$_2$), 1.92–1.85 (m, 2 H, CH$_2$CH$_2$CH$_2$).

Example 11
3-[[5-[[5-[4-(Methyl 2,3,4-tri-O-acetyl-1-deoxy-b-D-glucuronate) butyramino]-1H-indol-2-ylcarbonyl]amino]-1H-indol-2-yl]carbony 1]-1-(chloromethyl)-5-hydroxy-1,2-dihydro-3H-benz[e]indole (YW-249).

YW-249 was synthesized using a similar procedure as that described for YW-198 except that 38 was used to afford a yellow solid (15% yield). $^1$H NMR (DMF-d$_6$, ppm): 11.61 (s, 2 H, 2 NH), 10.20 (s, 1 H, CONH), 9.79 (s, 1 H, CONH), 5 8.38–7.27 (m, 13 H, Ar—H), 5.99–5.98 (d, 1 H, J=4.6 Hz, sugar C1—H), 5.22–5.20 (t, 1 H, J=3.1 Hz, sugar C2—H), 5.16–5.13 (m, 1 H, sugar C4—H), 4.91–4.86 (t, 1 H, J=8.7 Hz, NCHH), 4.77–4.73 (dd, 1 H, J=1.8, 11.4 Hz, CHHCl), 4.51–4.48 (m, 2 H, sugar C3—H, C5—H), 4.34–4.32 (m, 1 H, ClCH$_2$CH), 4.15–4.11 (dd, 1 H, J=3.4, 11.2 Hz, ClCHH), 3.98–3.92 (dd, 1 H, J=8.0, 11.1 Hz, ClCHH), 3.77 (s, 3 H, COOCH$_3$), 3.63–3.59 (t, 2 H, J=6.6 Hz, OCH$_2$), 2.50–2.46 (t, 2 H, J=7.3 Hz, COCH$_2$), 2.10 (s, 3 H, CH$_3$CO), 2.08 (s, 3 H, CH$_3$CO), 1.94–1.90 (m, 2 H, CH$_2$CH$_2$CH$_2$), 1.72 (s, 3 H, CH$_3$CO).

Example 12
3-[[5-[[5-[[5-[4-(Methyl 2,3,4-tri-O-acetyl-1-deoxy-b-D-glucuronate)butyramino]-1H-indo 1-2-ylcarbonyl]amino]-1H-indol-2-ylcarbonyl]amino]-1H-indol-2-yl]carbonyl]-1-(chloromethyl)-5-hydroxy-1,2-dihydro-3H-benz[e] indole (YW-258).

YW-258 was synthesized using a similar procedure as that described for YW-198 except that 40 was used to afford a yellow solid (8% yield). $^1$H NMR (DMF-d$_6$, ppm): 11.66 (s, 1 H, NH), 11.62 (s, 1 H, NH), 11.56 (s, 1 H, NH), 10.56 (brs, 1 H, OH), 10.25 (s, 1 H, CONH), 10.18 (s, 1 H, CONH), 9.82 (s, 1 H, CONH), 8.37–7.29 (m, 17 H, Ar—H), 5.99–5.98 (d, 1 H, J=4.4 Hz, sugar C1—H), 5.22–5.20 (t, 1 H, J=3.1 Hz, sugar C2—H), 5.15–5.12 (m, 1 H, sugar C4—H), 4.92–4.87 (t, 1 H, J=8.8 Hz, NCHH), 4.77–4.72 (dd, 1 H, J=1.8, 11.5 Hz, NCHH), 4.51–4.48 (m, 2 H, sugar C3—H, C5—H), 4.34–4.32 (m, 1 H, ClCH$_2$CH), 4.16–4.12 (dd, 1 H, J=3.4, 11.3 Hz, ClCHH), 3.99–3.93 (dd, 1 H, J=8.0, 11.2 Hz, ClCHH), 3.77 (s, 3 H, COOCH$_3$), 3.63–3.59 (t, 2 H, J=6.7 Hz, OCH$_2$, partially obscured by H$_2$O), 2.50–2.46 (t, 2 H, J=6.8 Hz, COCH$_2$), 2.11 (s, 3 H, CH$_3$CO), 2.08 (s, 3 H, CH$_3$CO), 1.95–1.91 (m, 2 H, CH$_2$CH$_2$CH$_2$), 1,73 (s, 3 H, CH$_3$CO).

Example 13
3-[[5-[[5-[[5-[4-(Hydroxy)butyramino]-1H-indol-2-ylcarbonyl]amino]-1H-indol-2-ylcarbonyl]amino]-1H-indol-2-yl]carbonyl]-1-(c)hloromethyl)-5-hydroxy-1,2-dihydro-3H-benz[e]indole (YW-259).

A solution of YW-258 (6.5 mg, 0.006 mmol) in DMF (2 mL) as treated with a solution of ethyl acetate saturated with hydrogen chloride (0.25 mL), and stirred for 3 h at room temperature. Solvent was removed in vacuo and the product was washed with ether to afford the target compound YW-258 (4.2 mg, 91%) as a yellow solid. $^1$H NMR (DMF-d$_6$, ppm) 11.77 (s, 1 H, NH), 11.67 (s, 1 H, NH), 11.62 (s, 1 H, NH), 10.54 (s, 1 H, Ar—OH), 10.31 (s, 1 H, CONH), 10.23 (s, 1 H, CONH), 9.82 (s, 1 H, CONH), 8.40–7.29 (m, 16 H, Ar—H), 6.54 (s, 1 H, Ar—H), 4.93–4.87 (t, 1 H, J=8.5 Hz, NCHH), 4.77–4.74 (dd, 1 H, J=1.6, 11.1 Hz, NCHH), 4.56–4.53 (t, 1 H, J=4.9 Hz, CH$_2$OH), 4.36–4.32 (m, 1 H, ClCH$_2$CH), 4.15–4.11 (dd, 1 H, J=3.5, 11.1 Hz, ClCHH), 3.98–3.93 (dd, 1 H, J=7.9, 11.2 Hz, ClCHH), 3.63–3.57 (q, 2 H, J=6.1, 11.4 Hz, CH$_2$OH), 2.51–2.47 (t, 2 H, J=7.5 Hz, COCH$_2$), 1.91–1.87 (m, 2 H, CH$_2$CH$_2$CH$_2$).

Example 14
3-[(5-Amino-1H-indol-2'-yl)carbonyl]-1-(chloromethyl)-5-hydroxy-1,2-dihydro-3H-benz[e]indole (YW-242).

5-Nitroindole-2-carboxylic acid (18 mg, 87 mmol) made from basic (NaOH) hydrolysis of ethyl 5-nitroindole-2-carboxylate (Eastman chemical Co.) followed neutralization using HCl was coupled to 41. The reaction mixture was stirred at room temperature overnight and purified by thin layer chromatography eluting with 50% hexane in ethyl acetate to give the coupled product. Without further characterization, the latter was dissolved DMF (0.5 mL). Ethyl acetate (5 mL) was added to the solution followed by 10% Pd/C (10 mg) and the reaction mixture was hydrogenated for 1 h at ambient temperature under 1 atm pressure. The product was filtered and the filter cake was washed with methanol (20 mL). The solvent was removed in vacuo and ether was added. The solid was filtered and washed to afford YW-242 (13 mg, 44% yield). mp>300° C. $^1$H NMR (DMF-d7, ppm): 11.16 (brs, 1, NH), 10.46 (s, 1, OH), 8.24–6.81 (m, 9, Ar—H), 4.84–4.79 (dd, 1, J=9.3, 11.1z, NHH), 4.71–4.67 (m, 3, NCHH, NH$_2$), 4.31–4.21 (m, 1, CH$_2$ClCHCH$_2$N), 4.18–4.12 (dd, 1, J=1.0, 18.7z, ClCHH), 3.93–3.88 (dd, 1, J=7.9, 11.2z, ClCHH).

Example 15
3-[[5-(Biotin-amino)-1H-indol-2'-yl]carbonyl]-1-(chloromethyl)-5-hydroxy-1,2-dihydro-3H-benz[e]indole (YW-235).

To a solution of YW-242 (2 mg, 5.1 mmol) in DMF (0.2 mL) was added N-hydroxysuccinimidobiotin (5.2 mg, 15.3 mmol) and the solution was stirred for 48 h at ambient temperature. The product was purified by thin layer chromatography eluting with ethyl acetate and methanol (4/1, v/v) to give YW-235 (1.5 mg, 48%) as a grey solid. $^1$H NMR (DMF-d7, ppm): 11.56 (brs, 1 H, NH), 10.55 (s, 1 H, OH), 9.91 (s, 1 H, NH), 8.25–7.21 (m, 9 H, Ar—H), 6.32 (s, 1 H, biotin NH), 6.24 (s, 1 H, biotin NH), 4.90–4.85 (t, 1 H, J=11.0 Hz, NHH), 4.74–4.70 (dd, 1 H, J=2.0, 11.0 Hz, NHH), 4.49–4.45 (m, 1 H, biotin H), 4.32–4.28 (m, 2 H, ClCH$_2$CHCH$_2$, biotin H), 4.14–4.10 (dd, 1 H, J=3.6, 11.1 Hz, CHHCl), 3.96–3.91 (dd, 1 H. J=7.8, 11.1 Hz, CHHCl), 3.20–3.27 (m, 1 H, biotin H), 2.45–2.41 (t, 2 H, J=7.7 Hz, COCH$_2$), 1.8–1.5 (m, 6 H, CO(CH$_2$)$_3$).

Example 16
Cephalothin-YW-242 Prodrug (YW-285).

Figure 10:
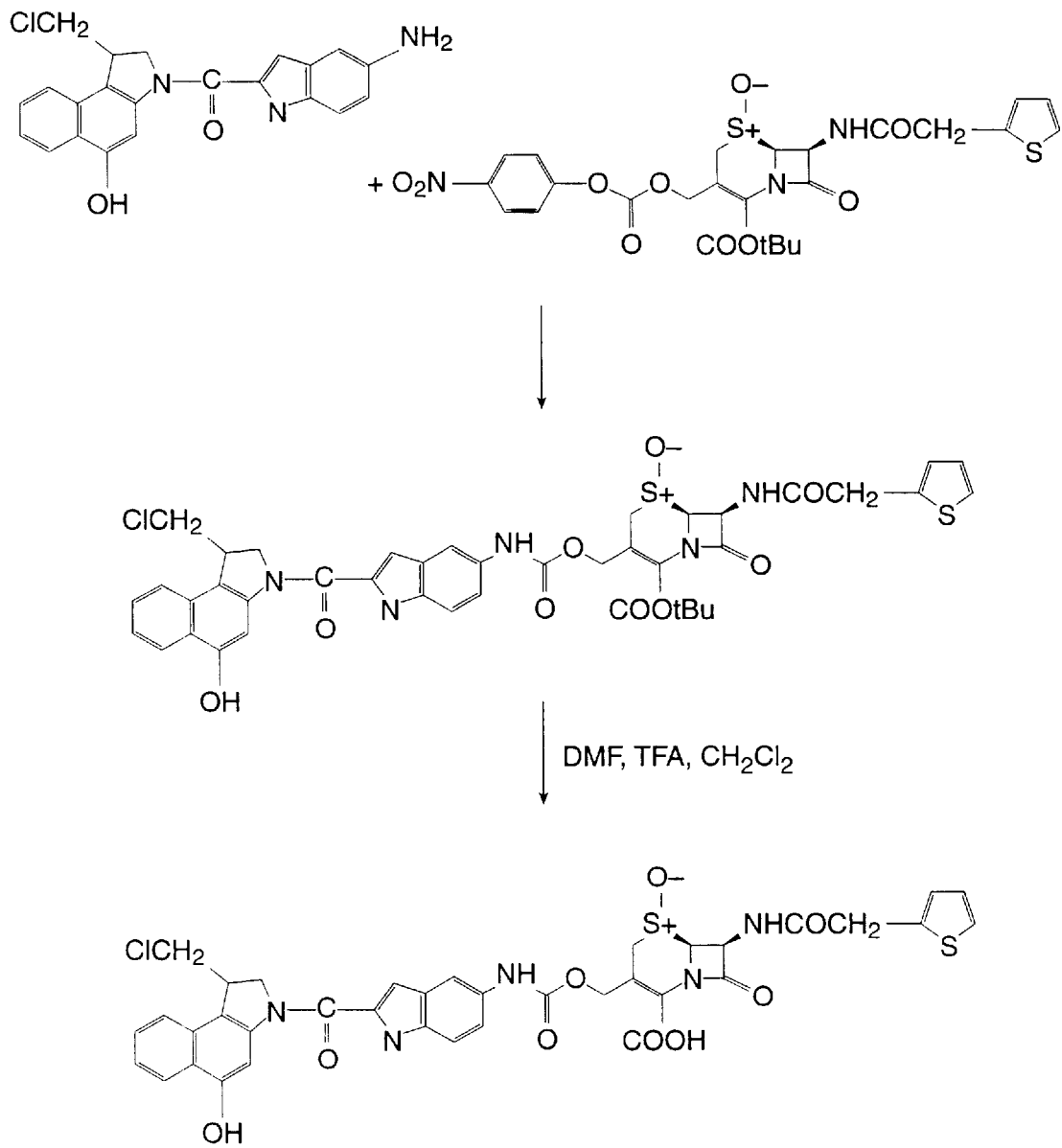
FIG. 10 shows the route of synthesis of cephem prodrug YW-285.

YW-242 (9 mg) in DMF (0.3 mL) was treated with tert-butyl-7b-(2-(thien-2-yl)acetamido)-3-[[[4-nitrophenoxy)carbonyl]oxy]methyl]-3-cephem-4- carboxylate 1-sulfoxide (15 mg) synthesized according to the reported procedure (FIG. 10, Rodrigues, et al., *Cancer Res.* 1995, 55:63), and the reaction mixture was stirred at room temperature overnight. The mixture was purified by thin layer chromatography using ethyl acetate and hexane (3/1, v/v) as eluent to afford 12 mg of product. 5 mg of the latter product was dissolved in DMF (0.2 mL) and dichloromethane (1 mL) and trifluroacetic acid (1 mL) was added sequentially. The reaction was stirred at room temperature for 2 h. Solvent was removed in vacuo and ether was added. The solid was filtered and washed with ether to afford YW-285 (3.7 mg). $^1$H NMR (DMF-d7, ppm): 11.63 (s, 1 H), 11.56 (s, 1 H), 11.50 (brs, 1 H), 8.28–8.23 (m, 1 H), 8.17–8.12 (m, 1 H), 8.07–8.01 (m, 1H, partially obscured by DMF), 7.94–7.91 (d, 1 H, J=8.5 Hz), 7.58–7.52 (m, 2 H), 7.46–7.38 (m, 3 H), 7.24 (s, 1 H), 7.05–6.99 (m, 2 H), 6.07–6.03 (dd, 1 H, J=4.8, 9.0 Hz), 5.40–5.37 (d, 1 H, J=13.2 Hz), 5.08–5.06 (d, 1 H, J=4.4 Hz), 4.90–4.0 (m, 1 H), 4.74–4.70 (d, 1 H, J=13 Hz), 4.35–4.27 (m, 1 H), 4.19–3.75 (m, 6 H).

Example 17

1, 2, 9, 9a-2-[[5-[(1H-benzofuran-2-ylcarbonyl)amino]-1H-indol-2-yl]carbonyl]tetrahydrocycloprop-a[c]-benz[e]indol-4-one (YW-211).

YW-199 (10 mg) was dissolved in DMF (0.5 mL) and triethylamine (0.5 mL), water (0.5 mL) and acetonitrile (0.5 mL) was added sequentially. The reaction mixture was stirred at room temperature for 30 min. Solvent was removed in vacuo and the product was washed with water. Ether was added and the solid was filtered and washed with ether to afford YW-211 (7 mg). $^1$H NMR (DMSO-d6, ppm): 11.71 (s, 1 H, NH),10.32 (s, 1 H, NH), 8.21–6.88 (m, 14 H, Ar—H), 4.66–4.62 (dd, 1 H, J=4.6, 10.0 Hz, NHH), 4.52–4.49 (d, 1 H, J=10.2 Hz, NHH), 3.05–2.95 (m, 1 H), 1.79–1.75 (dd, 1H, J=4.4, 7.9 Hz), 1.72–1.70 (t, 1H, J=4.8 Hz).

Example 18

1,2, 9, 9a-2-[5-[[5-(Acetamino)-1H-benzofuran-2-ylcarbonyl]amino]-1H-indol-2-yl]carbonyl]] tetrahydrocycloprop-a[c]-benz[e]indol-4-one (YW-213).

YW-213 was synthesized using a similar procedure as that described for YW-211 except that YW-201 was used to afford a grey solid (85% yield). $^1$H NMR (DMSO-d6, ppm): 11.77 (s, 1 H, NH), 11.45 (s, 1 H, NH),10.28 (s, 1 H, NH), 8.21–6.96 (m, 13 H, Ar—H), 4.66–4.61 (dd, 1 H, J=4.6, 10.0 Hz, NHH), 4.52–4.49 (d, 1 H, J=10.3 Hz, NHH), 3.05–2.95 (m, 1 H), 2.08 (s, 3 H), 1.77–1.73 (dd, 1H, J=4.4, 7.9 Hz), 1.72–1.70 (t, 1 H, J=4.8 Hz).

Example 19

3-[(4-Amino-1-methylpyrrole-2-yl)carbonyl]-1-(chloromethyl)-5-hydroxy-1,2-dihydro-3H-benz[e]indole (YW-284).

YW-286 was synthesized using a similar procedure as that described for YW-198 except that 1-methyl-5-nitropyrrole-2-carboxylic acid was used (85% yield). YW-286 (20 mg) was dissolved DMF (0.5 mL). Ethyl acetate (5 mL) was added to the solution followed by 10% Pd/C (10 mg) and the reaction mixture was hydrogenated for 1 h at ambient temperature under 1 atm pressure. The product was filtered and the filter cake was washed with methanol (20 mL). The solvent was removed in vacuo and ether was added. The solid was filtered and washed to afford YW-284 (15 mg). $^1$H NMR (DMSO-d6, ppm): 10.26 (s, 1 H, OH), 8.10–6.17 (m, 7 H, Ar—H), 4.51–4.41 (dd, 1 H, J=8.5, 11.6 Hz, NHH), 4.33–4.30 (d, 1 H, J=9.9 Hz, NCHH), 4.02–3.93 (m, 3 H, CH$_2$ClCHCH$_2$N, ClCHH), 3.76–3.66 (m, 4 H, ClCHH, CH$_3$).

Example 20

3-[(4-Acetamino-1-methylpyrrole-2-yl)carbony:L]-1-(chloromethyl)-5-hydroxy-1,2-dihydro-3H-benz[e]indole (YW-161).

YW-161 was synthesized using a similar procedure as that described for YW-198 except that 5-acetamino-1-methylpyrrole-2-carboxylic acid was used (25% yield). $^1$H NMR (DMF-d7, ppm): 10.49 (s, 1 H, OH), 9.88 (s, 1 H, NH), 8.23–6.64 (m, 7 H, Ar—H), 4.58–4.52 (dd, 1 H, J=8.5, 11.6 Hz, NHH), 4.47–4.30 (d, 1 H, J=9.9 Hz, NCHH), 4.15–4.03 (m, 3 H, CH$_2$ClCHCH$_2$N, ClCHH), 3.88–3.80 (m, 4 H, ClCHH, CH$_3$), 2.04 (s, 3 H, COCH$_3$).

Example 21

3-(4-Butyramido-1-methyl-2-pyrroleacryloylcarbonyl)-1-(chloromethyl)-5-hydroxy-1,2-dihydro-3H-benz[e]indole (YW-222).

YW-222 was synthesized using a similar procedure as that described for YW-198 except that 4-butyramido-N-methyl-2-pyrroleacrylic acid was used (20% yield). $^1$H NMR (DMF-d7, ppm): 10.46 (s, 1 H, OH), 9.77 (s, 1 H, NH), 8.22–6.81 (m, 9 H, Ar—H, CH═CH), 4.54–4.51 (m, 2 H, NCH$_2$), 4.28–4.20 (brs, 1 H, CH$_2$ClCHCH$_2$N), 4.10–4.06 (dd, 1 H, J=3.4, 11.2 Hz, ClCHH), 3.91–3.85 (dd, 1 H, J=8.6, 11.1 Hz, ClCHH), 3.79 (s, 3 H, NCH$_3$). 2.31–2.27 (t, 2 H, J=14.6 Hz, CH$_3$CH$_2$CH$_2$), 1.69–1.63 (m, 2 H, CH$_3$CH$_2$CH$_2$), 0.95–0.91 (t, 3 H, J=14.6 Hz, CH$_3$CH$_2$CH$_2$).

Example 22

Cytotoxicity to Cancer Cells

Some of the new compounds were tested for their cytotoxicity against cancer cells. U937 cells were used to determine the IC$_{50}$ values. The assay was set up in triplicate in 96 well flat bottom microtiter plates. All cells are seeded at 5×103 cells/well in RPMI-1640 plus 10% FCS. Drugs were added and the total volume was adjusted to 0.2 mL/well. Total incubation time was 48 h with the addition of $^3$H-thymidine for the last 24 h of incubation. The assay was harvested and counted with the packard Matrix 96 beta counter. The results were expressed as the percent growth inhibition calculated from the percent decrease in cpm of treated cells relative to the untreated controls.

Figure 9:
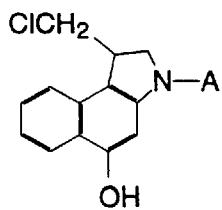
FIG. 9 shows the $IC_{50}$ values of the invented compounds against U937 cells in vitro.

The results are shown in FIG. 9.

Example 23

Synthesis of YW-242-monoclonal Antibody Conjugates

Figure 11:
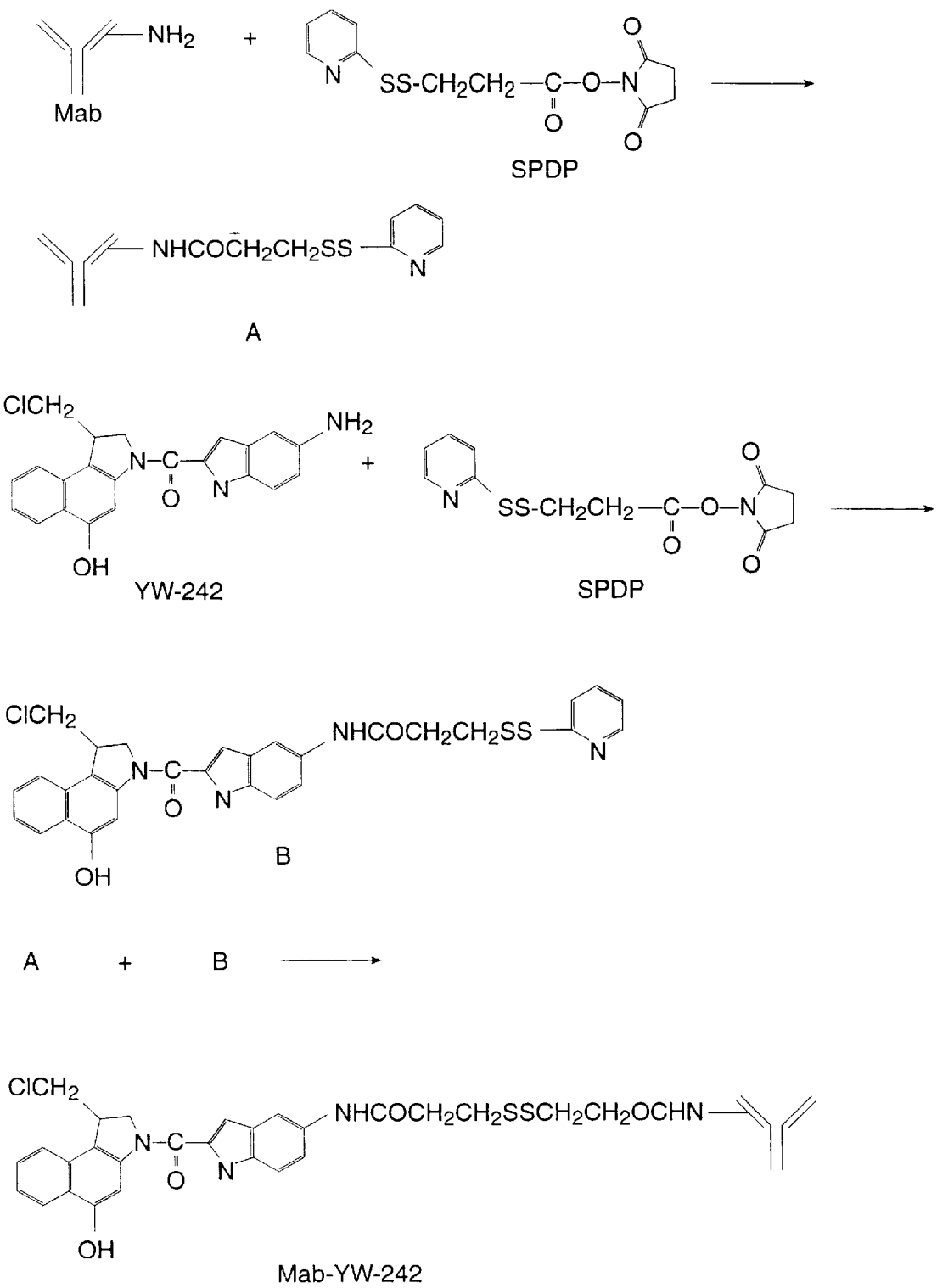
FIG. 11 shows the route of synthesis of YW-242-monoclonal antibody conjugates.

YW-242 exerts its antitumor activity by binding in the minor groove of DNA. Therefore the drug has to be released from the Mab-drug conjugate after entering cells. A disulfide linker meets this requirement, and is used to connect YW-242 and MAb 3A5 (FIG. 11)

a). Thiolation of Mabs. Mab 3A5 was made according to the reported procedure. (Li et al., *Acta Pharmaceutica Sinica* 1993, 28:260). 3-(2-Pyridyldithio)propionic acid N-hydroxysuccinimide ester (SPDP, 0.152 mg) in ethanol (50 μL) was added to Mab 3A5 (2 mg) in PBS (2 mL) and the reaction mixture was incubated for 30 min at 37° C. The mixture was cooled to 0° C. and then treated with dithiotheritol (0.45 mg in 50 μL of PBS) for 15 min at 4° C. The thiolated Mab was separated by gel filtration chromatography (Sephadex-G 25).

b). Thiolation of YW-242. YW-242 (0.5 mg in 83 μL of DMF) was added to SPDP (5.3 mg, 1 mol. equivalent to YW-242, in 0.263 mL of ethanol) and the reaction mixture was incubated for 30 min at 37° C. The product was used without further purification.

c). Conjugation of MAb and the drug. Thiolated YW-242 was added to the thiolated Mabs in PBS and the reaction mixture was allowed to react overnight at 4° C. The reaction mixture was then dialyzed in PBS (1000 mL) for 6 h (PBS was changed every 2 h). The amount of drug bound to Mab was analyzed by UV absorbance and the concentration was calculated. The number of drug molecules conjugated per Mab is 2.7.

Example 24
Cytotoxicity Studies of the YW-242-monoclonal Antibody Conjugates against Liver Cancer HepG2 Cells The conjugates were tested in vitro against human liver cancer HepG2 cells. $IC_{50}$ values for cell proliferation were determined by incorporation of $^3$H-thymidine. $4\times10^4$ of trypsinized cells in 0.1 mL of DMEM medium containing 10% of heat-inactivated FCS were added to each well of 96-well microtiter plates and incubated for 4 h at 37° C. to allow attachment of the cells. Drugs in 10 μL of PBS were added and incubated for 1 h at 37° C. Medium was removed and the cells were washed with PBS (0.2 mL). Fresh medium (0.1 mL) and $^3$H-thymidine (10 μL) were added. The cells were incubated overnight at 37° C. The cells were treated with trypsin-EDTA for 15 min at 37° C. and then harvested using a micromate 196 harvester. Radioactivity was counted and $IC_{50}$ values were determined. The results are shown in Table 3.

The immunoconjugate Mab-YW-242 is 2.5-fold less toxic than the free drug YW-242. This reduced cytotoxicity is expected because the Mab-drug conjugate is usually less toxic than the free drug in this kind of assay. These results indicates that the Mab-drug conjugate binds to the cell and the free drug is released inside cells. The Mab-drug conjugate is more than 10-fold more potent than doxorubicin.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of the formula:

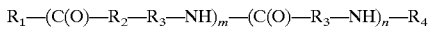

wherein:

$R_1$ is selected from the group consisting of:

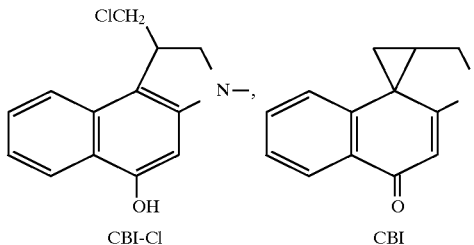

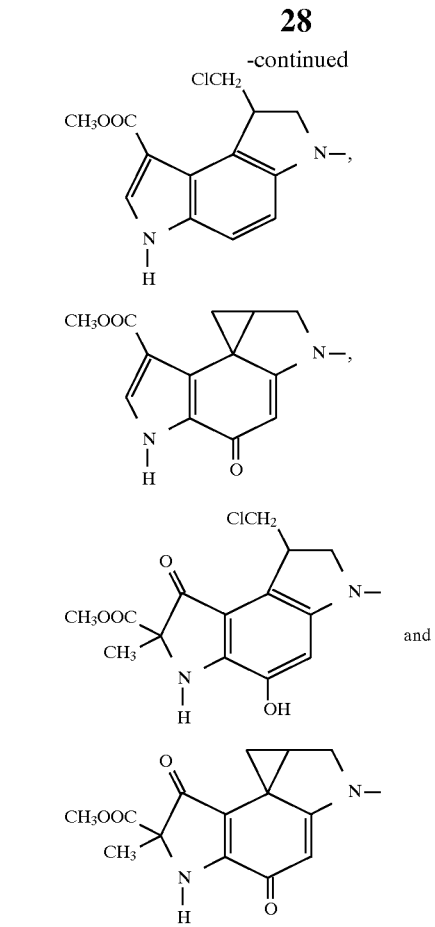

wherein:
  each $R_2$ is the same or different and is a valence bond or a divalent hydrocarbyl radical;
  each $R_3$ is the same or different and is a divalent monocyclic or bicyclic heterocyclic aromatic radical;
  m and n are integers from 0 to 3, where m+n≦3; and
  $R_4$ is independently:
    Z where Z is either X or Y, where X is a structure of the Formula I,

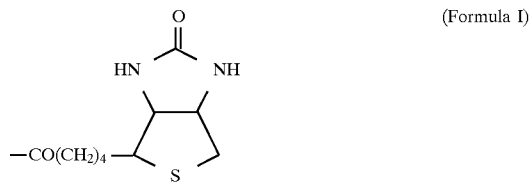

and Y is a structure of the Formula II,

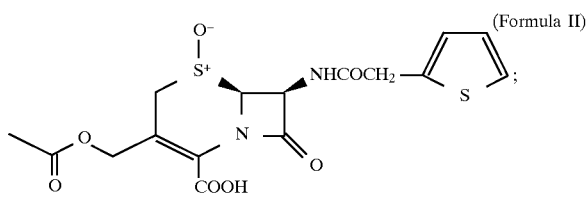

or $C(O)R_5$, where $R_5$ is independently:
  $NH_2$; $C_1$–$C_6$ alkyl; $C_1$–$C_6$ hydroxyalkyl; $C_1$–$C_6$ hydroxycycloalkyl; hydroxyphenyl; hydroxymethylphenyl; hydroxybenzyl; $C_1$–$C_6$ aminoalkyl; $C_1$–$C_6$ alkylamino$C_1$–$C_6$alkyl; di-($C_1$–$C_6$)- alkylaminoC$_1$–C$_6$alkyl; C$_1$–C$_6$ ureidoalkyl; a C$_1$–C$_6$ alkyl group carrying a positively charged substituent selected from the group consisting of an amidinium group, a guanadinium group, a secondary aminium salt, a tertiary aminium salt, a quaternary ammonium salt, a sulfonium group, and a phosphonium group; C$_1$–C$_6$ alkyl-NHZ; C$_1$–C$_6$ cycloalkyl-NHZ; phenyl-NHZ; —CH$_2$-phenyl-NHZ; -phenyl-CH$_2$—NHZ; C$_1$–C$_6$ alkyl-OR$_6$; C$_1$–C$_6$ cycloalkyl-OR$_6$; phenyl-OR$_6$; —CH$_2$-phenyl-OR$_6$; or -phenyl-CH$_2$—OR$_6$, where R$_6$ is selected from the group consisting of:

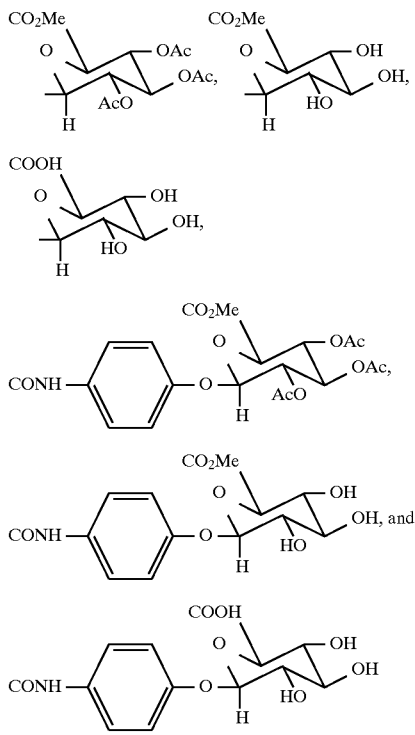

provided that, when R$_5$ is NH$_2$ or C$_1$–C$_6$ alkyl:
when m+n=2 and both R$_3$'s are indole.

2. The compound of claim 1, wherein R$_2$ is a valence bond or a divalent hydrocarbyl radical selected from the group consisting of a C$_1$–C$_6$ alkyl, a C$_1$–C$_6$ alkenyl, a C$_1$–C$_6$ alkynyl and an ortho-, meta- or para-linked aromatic group.

3. The compound of claim 2, wherein R$_2$ is CH$_2$, CH$_2$CH$_2$, CH=CH (trans or cis), or —C≡C—.

4. The compound of claim 1, wherein R$_3$ is selected from the group consisting of indole, substituted indole, benzofuran, substituted benzofuran, benzothiophene, substituted benzothiophene, pyrrole, substituted pyrrole, imidazole, triazole, pyrazole, thiazole, thiophene, furan, isoxazole and oxazole.

5. The compound of claim 1, wherein R$_4$=Z.

6. The compound of claim 1, wherein R$_4$ is —C(O)—R$_5$ and R$_5$ is selected from the group consisting of C$_1$–C$_6$ hydroxyalkyl, C$_1$–C$_6$ hydroxycycloalkyl, hydroxyphenyl, hydroxymethylphenyl and hydroxybenzyl.

7. The compound of claim 1, wherein R$_4$ is —C(O)—R$_5$ and R$_5$ is selected from the group consisting of C$_1$–C$_6$ aminoalkyl, C$_1$–C$_6$ alkylaminoC$_1$–C$_6$alkyl, di-(C$_1$–C$_6$)-alkylaminoC$_1$–C$_6$ alkyl and C$_1$–C$_6$ ureidoalkyl.

8. The compound of claim 7, wherein R$_5$ is an ω-aminoalkyl, an ω-alkylaminoalkyl, an ω-dialkylaminoalkyl or an ω-ureidoalkyl.

9. The compound of claim 1 wherein R$_4$ is —C(O)—R$_5$ and R$_5$ is an alkyl group carrying a positively charged substituent selected from the group consisting of an amidinium group, a guanadinium group, a secondary aminium salt, a tertiary aminium salt, a quaternary ammonium salt, a sulfonium group, and a phosphonium group.

10. The compound of claim 9, wherein the positively charged substituent is on the terminal carbon of the alkyl group.

11. The compound of claim 1, wherein R$_4$ is —C(O)—R$_5$ and R$_5$ is selected from the group consisting of C$_1$–C$_6$ alkyl-NHZ, C$_1$–C$_6$ cycloalkyl-NHZ, phenyl-NHZ, —CH$_2$-phenyl-NHZ and -phenyl-CH$_2$—NHZ.

12. The compound of claim 11, wherein the group NHZ is on the terminal carbon of R$_5$.

13. The compound of claim 1, wherein R$_4$ is —C(O)—R$_5$ and R$_5$ is selected from the group consisting of C$_1$–C$_6$ alkyl-OR$_6$, C$_1$–C$_6$ cycloalkyl-OR$_6$, phenyl-OR$_6$, —CH$_2$-phenyl-OR$_6$ and -phenyl-CH$_2$—OR$_6$.

14. The compound of claim 13, wherein the —OR$_6$ substituent is on the terminal carbon atom of R$_5$.

15. The compound of claim 1, where m=1; R$_2$ is selected from the group consisting of a valence bond, CH$_2$, CH$_2$CH$_2$, CH=CH (trans or cis), or —C≡C—; and R$_3$ is selected from the group consisting of indole, benzofuran, pyrrole, imidazole and furan.

16. The compound of claim 15, wherein R$_4$ is —C(O)13 R$_5$ and R$_5$ is selected from the group consisting of C$_1$–C$_6$ hydroxyalkyl, C$_1$–C$_6$ hydroxycycloalkyl, hydroxypenyl, hydroxymethylphenyl and hydroxybenzyl.

17. The compound of claim 15, wherein R$_4$ is —C(O)—R$_5$ and R$_5$ is selected from the group consisting of C$_1$–C$_6$ alkyl-NHZ, C$_1$–C$_6$ alkyl-NHZ, C$_1$–C$_6$ cycloalkyl-NHZ, phenyl-NHZ, —CH$_2$-phenyl-NHZ and -phenyl-CH$_2$—NHZ.

18. The compound of claim 17, wherein the group NHZ is on the terminal carbon of R$_5$.

19. The compound of claim 15, wherein R$_4$ is —C(O)—R$_5$ and R$_5$ is selected from the group consisting of C$_1$–C$_6$ alkyl-OR$_6$, C$_1$–C$_6$ cycloalkyl-OR$_6$, phenyl-OR$_6$, —CH$_2$-phenyl-OR$_6$ and -phenyl-CH$_2$—OR$_6$.

20. The compound of claim 19, wherein the —OR$_6$ substituent is on the terminal carbon atom of R$_5$.

21. The compound of claim 1, wherein:
R$_1$ is selected from the group consisting of:

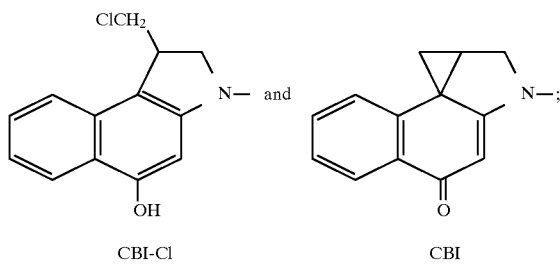

CBI-Cl                CBI

R$_4$ is —C(O)—R$_5$; and
R$_5$ is selected from the group consisting of C$_1$–C$_6$ hydroxyalkyl, C$_1$–C$_6$ hydroxycycloalkyl, hydroxyphenyl, hydroxymethylphenyl, hydroxybenzyl, C$_1$–C$_6$ alkyl-NHZ, C$_1$–C$_6$ cycloalkyl-NHZ, phenyl-NHZ, —CH$_2$-phenyl-NHZ, -phenyl-CH$_2$—NHZ, C$_1$–C$_6$ alkyl-OR$_6$, C$_1$–C$_6$ cycloalkyl-OR$_6$, phenyl-OR$_6$, —CH$_2$-phenyl-OR$_6$ and -phenyl-CH$_2$—OR$_6$.

22. The compound of claim 21, wherein m=1 and R$_2$ is a divalent hydrocarbyl radical selected from the group consisting of a C$_1$–C$_6$ alkyl, a C$_1$–C$_6$ alkenyl, a C$_1$–C$_6$ alkynyl and an ortho-, meta- or para-linked aromatic group.

23. The compound of claim 22, where $R_5$ is $C_1$–$C_6$ hydroxyalkyl, $C_1$–$C_6$ hydroxycycloalkyl, hydroxyphenyl, hydroxymethylphenyl or hydroxybenzyl.

24. The compound of claim 21, where $R_5$ is $C_1$–$C_6$ alkyl-NHZ, $C_1$–$C_6$ alkyl-NHZ, $C_1$–$C_6$ cycloalkyl-NHZ, phenyl-NHZ, —$CH_2$-phenyl-NHZ or -phenyl-$CH_2$—NHZ.

25. The compound of claim 21, where $R_5$ is $C_1$–$C_6$ alkyl-$OR_6$, $C_1$–$C_6$ cycloalkyl-$OR_6$, phenyl-$OR_6$, —$CH_2$-phenyl-$OR_6$ or -phenyl-$CH_2$-$OR_6$.

26. A compound of the formula:

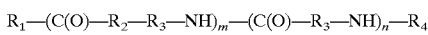

wherein:

$R_1$ is selected from the group consisting of:

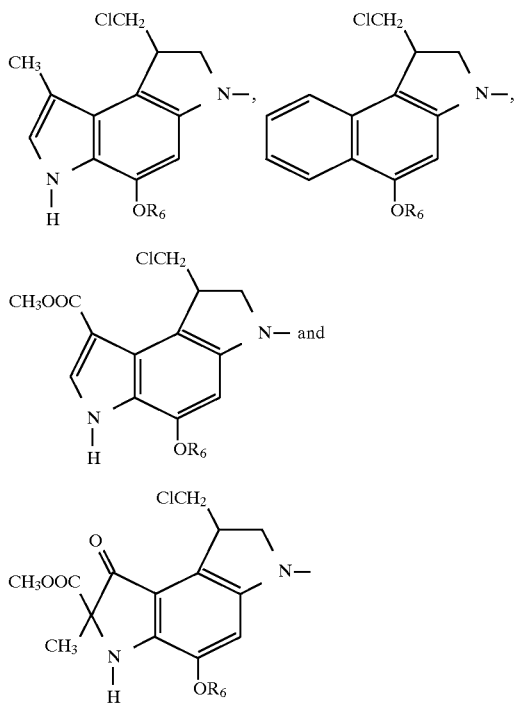

wherein:

each $R_2$ is the same or different and is a valence bond or a divalent hydrocarbyl radical;

each $R_3$ is the same or different and is a divalent monocyclic or bicyclic heterocyclic aromatic radical;

m and n are integers from 0 to 3, where m+n≦3; and $R_4$ is $C(O)R_5$, where $R_5$ is independently:

$NH_2$; $C_1$–$C_6$ alkyl; $C_1$–$C_6$ hydroxyalkyl; $C_1$–$C_6$ hydroxycycloalkyl; hydroxyphenyl; hydroxymethylphenyl; hydroxybenzyl; $C_1$–$C_6$ aminoalkyl; $C_1$–$C_6$ alkylamino$C_1$–$C_6$ alkyl; di-($C_1$–$C_6$)-alkylamino$C_1$–$C_6$ alkyl; $C_1$–$C_6$ ureidoalkyl or $C_1$–$C_6$ alkyl group carrying a positively charged substituent selected from the group consisting of an amidinium group, a guanadinium group, a secondary aminium salt, a tertiary aminium salt, a quaternary ammonium salt, a sulfonium group, and a phosphonium group; and $R_6$ is selected from the group consisting of

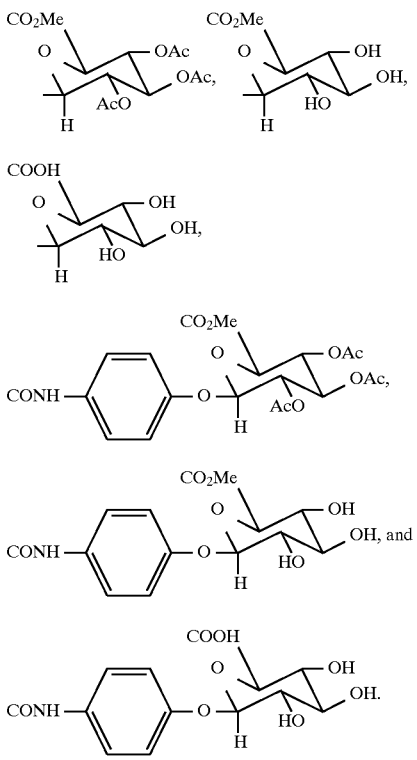

27. The compound of claim 26, wherein $R_2$ is a valence bond or a divalent hydrocarbyl radical selected from the group consisting of a $C_1$–$C_6$ alkyl, a $C_1$–$C_6$ alkenyl, a $C_1$–$C_6$ alkynyl and an ortho-, meta- or para-linked aromatic group.

28. The compound of claim 27, wherein $R_2$ is $CH_2$, $CH_2CH_2$, CH=CH (trans or cis), or —C≡C—.

29. The compound of claim 26, wherein $R_3$ is selected from the group consisting of indole, substituted indole, benzofuran, substituted benzofuran, benzothiophene, substituted benzothiophene, pyrrole, substituted pyrrole, imidazole, triazole, pyrazole, thiazole, thiophene, furan, isoxazole and oxazole.

30. A compound of the formula:

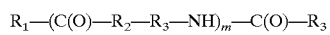

wherein:

$R_1$ is selected from the group consisting of:

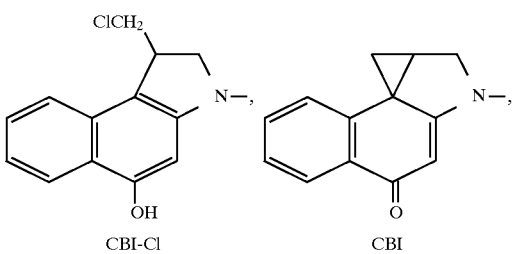

CBI-Cl        CBI

-continued

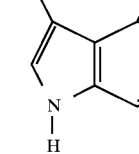

wherein:
each $R_2$ is the same or different and is a valence bond or a divalent hydrocarbyl radical;
each $R_3$ is the same or different and is a divalent monocyclic or bicyclic heterocyclic aromatic radical;
m is an integer from 0 to 3.

31. The compound of claim 30, wherein $R_2$ is a valence bond or a divalent hydrocarbyl radical selected from the group consisting of a $C_1$–$C_6$ alkyl, a $C_1$–$C_6$ alkenyl, a $C_1$–$C_6$ alkynyl and an ortho-, meta- or para-linked aromatic group.

32. The compound of claim 31, wherein $R_2$ is $CH_2$, $CH_2CH_2$, CH=CH (trans or cis), or —C≡C—.

33. The compound of claim 30, wherein $R_3$ is selected from the group consisting of indole, substituted indole, benzofuran, substituted benzofuran, benzothiophene, substituted benzothiophene, pyrrole, substituted pyrrole, imidazole, triazole, pyrazole, thiazole, thiophene, furan, isoxazole and oxazole.

34. A compound of the formula:

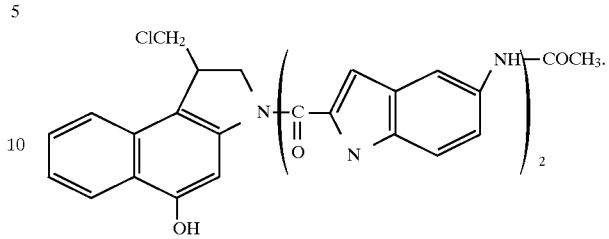

35. A compound of the formula:

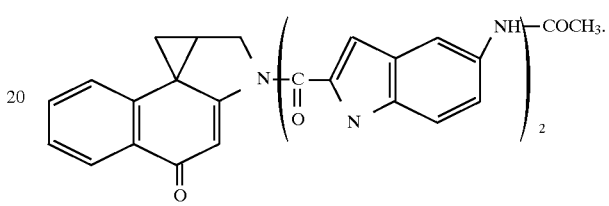

36. A pharmaceutical composition comprising a pharmaceutically acceptable non-toxic excipient and a therapeutically effective amount of a compound of claim 1, or a pharmaceutically acceptable salt thereof.

37. A pharmaceutical composition comprising a pharmaceutically acceptable non-toxic excipient and a therapeutically effective amount of a compound of claim 13, or a pharmaceutically acceptable salt thereof.

38. A pharmaceutical composition comprising a pharmaceutically acceptable non-toxic excipient and a therapeutically effective amount of a compound of claim 26, or a pharmaceutically acceptable salt thereof.

39. A method of controlling the growth of a tumor in a patient comprising adminstering to the patient an effective amount of a compound of claim 1 and pharmaceutically acceptable excipients.

40. A method of treating a bacterially mediated disease in a patient comprising adminstering to the patient an effective amount of a compound of claim 1 and pharmaceutically acceptable excipients.

41. A method for alkylating specific DNA sequences in vivo comprising adminstering to a patient in need of such alkylating an effective amount of a compound of claim 1.

* * * * *

UNITED STATES PATENT AND TRADEMARK OFFICE
CERTIFICATE OF CORRECTION

PATENT NO. : 5,843,937
DATED : December 1, 1998
INVENTOR(S) : Yuqiang Wang et al.

It is certified that error appears in the above-identified patent and that said Letters Patent is hereby corrected as shown below:

Column 28, first chemical diagram should read:

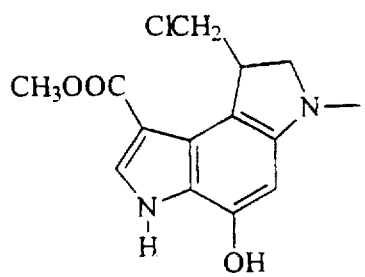

Column 29, lines 41-42, should read: "...provided that, when $R_5$ is $NH_2$ or $C_1$-$C_6$ alkyl: $R_1$ is not CBI or CBI-Cl when m+n=2 and both $R_3$'s are indole."

Column 30, lines 24-26, should read: "16. The compound of claim 15. wherein $R_4$ is -C(O)-$R_5$ and $R_5$ is selected from the group consisting of $C_1$-$C_6$ hydroxyalkyl, $C_1C_6$ hydroxyphenyl--.

UNITED STATES PATENT AND TRADEMARK OFFICE
CERTIFICATE OF CORRECTION

PATENT NO. : 5,843,937
DATED : December 1, 1998
INVENTOR(S) : Yuqiang Wang et al Page 2 of 6

It is certified that error appears in the above-identified patent and that said Letters Patent is hereby corrected as shown below:

Column 33, first chemical diagram should read:

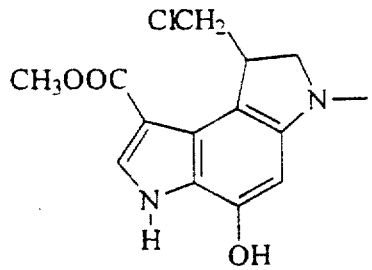

Claim 42. should be inserted to read: "42. A method of making a compound of formula $R_1$-(C(O)-$R_2$-$R_3$-NH)$_m$-(C(O)-$R_3$-NH)$_n$-$R_4$, said method comprising:

(a)    activating with a carboxyl group activating reagent, a carboxylic acid of formula:

$$HO\text{-}(C(O)\text{-}R_2\text{-}R_3\text{-}NH)_m\text{-}(C(O)\text{-}R_3\text{-}NH)_n\text{-}R_4$$

wherein:

each $R_2$ is the same or different and is a valence bond or a divalent hydrocarbyl radical;

each $R_3$ is the same or different and is a divalent monocyclic or bicyclic heterocyclic aromatic radical;

UNITED STATES PATENT AND TRADEMARK OFFICE
CERTIFICATE OF CORRECTION

PATENT NO. : 5,843,937           Page 3 of 6
DATED      : December 1, 1998
INVENTOR(S) : Yuqiang Wang et al It is certified that error appears in the above-identified patent and that said Letters Patent is hereby corrected as shown below:

m and n are integers from 0 to 3, where m + n ≤ 3; and $R_4$ is independently:

$C(O)R_5$, where $R_5$ is independently:

$NH_2$; $C_1$-$C_6$ alkyl; $C_1$-$C_6$ hydroxyalkyl; $C_1$-$C_6$ hydroxycycloalkyl; hydroxyphenyl; hydroxymethylphenyl; hydroxybenzyl; $C_1$-$C_6$ aminoalkyl; $C_1$-$C_6$ alkylamino$C_1$-$C_6$alkyl; di-($C_1$-$C_6$)-alkylamino$C_1$-$C_6$alkyl; $C_1$-$C_6$ ureidoalkyl; $C_1$-$C_6$ alkyl group carrying a positively charged substituent; $C_1$-$C_6$ alkyl-$OR_6$, $C_1$-$C_6$ cycloalkyl-$OR_6$, phenyl-$OR_6$, -$CH_2$-phenyl-$OR_6$ or -phenyl-$CH_2$-$OR_6$, wherein:

UNITED STATES PATENT AND TRADEMARK OFFICE
CERTIFICATE OF CORRECTION

PATENT NO. : 5,843,937
DATED : December 1, 1998
INVENTOR(S) : Yuqiang Wang et al It is certified that error appears in the above-identified patent and that said Letters Patent is hereby corrected as shown below:

$R_6$ is selected from the group consisting of

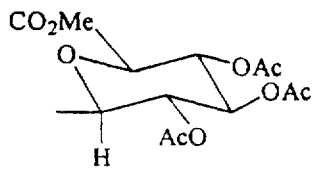 , 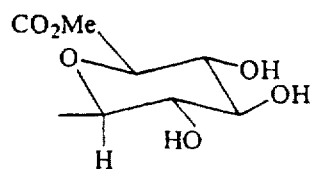 , 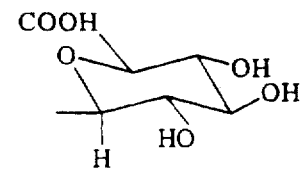

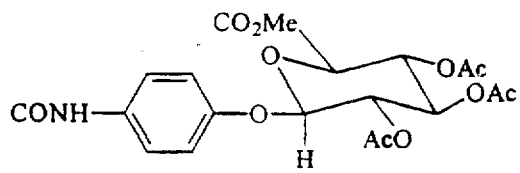 , 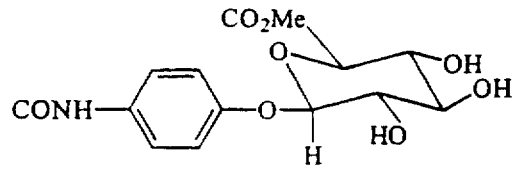

and 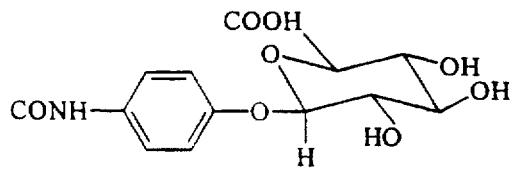 ;

UNITED STATES PATENT AND TRADEMARK OFFICE
CERTIFICATE OF CORRECTION

PATENT NO. : 5,843,937          Page 5 of 6
DATED     : December 1, 1998
INVENTOR(S) : Yuqiang Wang et al It is certified that error appears in the above-identified patent and that said Letters Patent is hereby corrected as shown below:

(b)  reacting the activated acid with an amine of formula $R_1$-H, wherein $R_1$ is selected from the group consisting of:

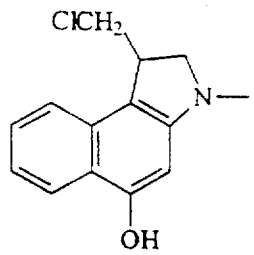

CBI-Cl

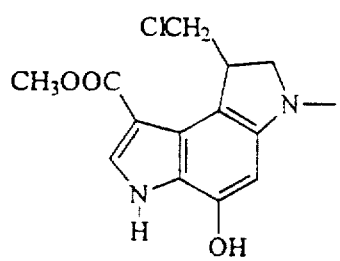 and 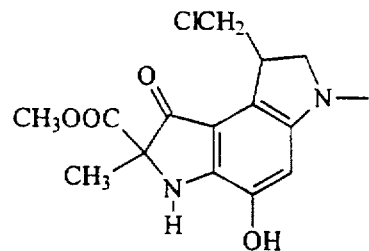

UNITED STATES PATENT AND TRADEMARK OFFICE
CERTIFICATE OF CORRECTION

PATENT NO. : 5,843,937
DATED : December 1, 1998
INVENTOR(S) : Yuqiang Wang et al It is certified that error appears in the above-identified patent and that said Letters Patent is hereby corrected as shown below:

provided that, when $R_5$ is $NH_2$ or $C_1$-$C_6$ alkyl:

$R_1$ is not CBI-Cl when m + n = 2 and both $R_3$'s are indole;

(c) optionally reacting the product of step (b) with a base; and (d) isolating the desired compound.

Signed and Sealed this

Twenty-eighth Day of March, 2000

Attest:

Q. TODD DICKINSON

*Attesting Officer*      *Commissioner of Patents and Trademarks*